(12) United States Patent
Iwata

(10) Patent No.: US 6,319,956 B1
(45) Date of Patent: Nov. 20, 2001

(54) LINEAR POLYAMINE COMPOUNDS AND POLYAMINE BASED ANTI-TUMOR AGENTS

(75) Inventor: Masaaki Iwata, Wako (JP)

(73) Assignee: Riken (JP)

( * ) Notice: Subject to any disclaimer, the term of this patent is extended or adjusted under 35 U.S.C. 154(b) by 0 days.

(21) Appl. No.: 09/468,408

(22) Filed: Dec. 20, 1999

(30) Foreign Application Priority Data

Dec. 21, 1998 (JP) .................................................. 10-363329

(51) Int. Cl.[7] ........................... A61K 31/13; A61K 31/18
(52) U.S. Cl. ........................ 514/674; 514/604; 564/82; 564/512
(58) Field of Search ...................... 564/512, 82; 514/674, 514/604

(56) References Cited

U.S. PATENT DOCUMENTS 5,109,024 * 4/1992 Prakash et al. ........................ 514/674
5,719,193 * 2/1998 Bowlin et al. ......................... 514/673

* cited by examiner

Primary Examiner—Peter O'Sullivan
(74) Attorney, Agent, or Firm—Burns, Doane, Swecker & Mathis, L.L.P.

(57) ABSTRACT

Nobel polyamine compounds and polyamine compounds having carcinostatic action are provided. There are also provided anticancer agents containing as active ingredient at least one of polyamine compounds represented by the following Formula (I) or (III) and/or pharmaceutically acceptable salts thereof.

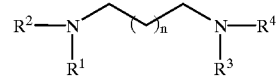

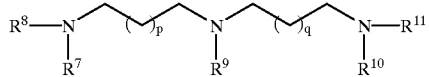

Specifically, there are provided anticancer agents containing as active ingredient at least one of 1,18-bis(ethylamino)-5,14-diazaoctadecane, 1,16-bis(cyclopropylmethylamino)-5,12-diazahexadecane, 1,17-bis(cyclopropylmethylamino)-5,13-diazaheptadecane and/or pharmaceutically acceptable salts thereof.

7 Claims, 3 Drawing Sheets

LINEAR POLYAMINE COMPOUNDS AND POLYAMINE BASED ANTI-TUMOR AGENTS

BACKGROUND OF THE INVENTION

1. Field of the Invention

The present invention relates to novel polyamine compounds and polyamine compounds having carcinostatic action.

2. Description of Related Art

Cancer accounts for the largest statistical portion of causes of death. It is one of the most difficult diseases to be cured, for which an establishment of an effective therapy is required. Currently, treatment is performed by using surgical therapy, immunological therapy, physiotherapy, chemotherapy and gene therapy individually or in a combination thereof. Cancer, which develops in any body tissues, is extremely diverse in appearance due to functions unique to each tissue, and can never be completely cured only by symptomatic therapies. Furthermore, drug resistance acquired by cancer cells after multiple uses of agents is a serious problem in chemotherapy. Therefore, development of anticancer agents that act with a novel mechanism has been strongly required.

One of the studies that can be a basis for new therapies in the development of anticancer agents is the study of the carcinostatic action of polyamine compounds. Polyamines are low molecular-weight compounds that can be found in cells of all species. Since polyamines considerably increase in concentration during proliferation and division of cells (C. W. Tabor and H. Tabor, Ann. Rev. Biochem., 53, pp.749–790 (1984) and L. J. Marton and D. R. Morris, "Inhibition of Polyamine Metabolism" (P. P. McCann, A. E. Pegg and A. Sjoerdsma eds.)), their relationship with these biochemical processes has long been noted. As studies progress, many aspects such as expression stages and roles of polyamines in the cell cycle, biosynthesis processes, types and functions of related enzymes and polyamine-decomposing enzymes and their metabolites have come to light. In recent years, existing sites and nucleotide sequences on DNA involved in the production of these enzymes have been elucidated, which continues to attract the attention of researchers engaged in molecular biology.

These studies have revealed that polyamines are involved in proliferation and division of cells. Since cancer is a type of abnormal cell proliferation, there is suggested a possibility that polyamines can control cancer. Therefore, from the viewpoint that if it is possible to block biosynthesis pathways of polyamines or accelerate metabolism of reserved polyamines, cell proliferation can be inhibited, which may result in carcinostatic effect. Therefore, many enzyme inhibitors have been developed as anticancer agents. The first report of polyamine anticancer agents was made by R. J. Bergeron et al. (J. Med. Chem. 31:1183–1190 (1988)). Since then, they have pursued the investigation of the action mechanism and the correlation between structure and activity of polyamines, thereby contributing to the orientation of molecular design of polyamine anticancer agents. They have also provided a major driving force for many researchers stimulated by their study to turn to the development of polyamine anticancer agents.

With the success of these studies, clinical studies of BE333 as an anticancer agent began a few years ago. Since then, steady steps have been taken towards development of chemotherapeutic agents. Polyamines having an extremely low molecular weight and a simple structure are involved in the cell proliferation process, where macromolecules such as nucleic acid and protein are fully operating, and play a major role of functional regulation. From this fact, it can be considered to be highly possible that more useful polyamine anticancer agents can be developed. Therefore, there are expected further development of polyamine compounds, study of structures and actions of existing and novel polyamine compounds, investigation of action mechanisms and study of the correlation between structure and activity and so forth, and how to apply results of these studies to development of anticancer agents is considered a problem.

An object of the present invention is to provide novel polyamine compounds having much potential for the development of anticancer agents, in particular, to provide novel polyamine compounds by using a method of systematically synthesizing linear polyamine derivatives in order to facilitate detection of structural factors and specificity influencing on physiological activity of polyamines to be produced. Another object of the present invention is to provide polyamine compounds having carcinostatic action.

SUMMARY OF THE INVENTION

The present invention relates to polyamine compounds represented by the following Formula (I) and pharmaceutically acceptable salts thereof.

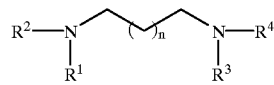

(I)

In Formula (I), n is an integer of 1–8, $R^1$ represents a hydrogen atom or a p-toluenesulfonyl group, $R^2$ represents an ethyl group or a group represented by the following Formula (II), $R^3$ represents a hydrogen atom or a p-toluenesulfonyl group, and $R^4$ represents an ethyl group or a group represented by the following Formula (II).

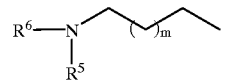

(II)

In Formula (II), m is 1 or 2, $R^5$ represents a hydrogen atom or a p-toluenesulfonyl group, $R^6$ represents a hydrogen atom, an ethyl group, an aldehyde group, or a cyclopropylmethyl group, or $R^5$ and $R^6$ form a phthaloyl group.

The present invention further relates to polyamine compounds represented by the following Formula (III) and pharmaceutically acceptable salts thereof.

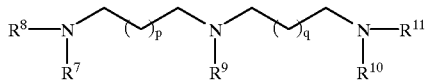

(III)

In Formula (III), p is 1, q is 1 or 2, $R^7$ represents a hydrogen atom or a p-toluenesulfonyl group, $R^8$ represents a hydrogen atom, an ethyl group, an aldehyde group, a cyclopropylmethyl group or a group represented by the following Formula (IV), or $R^7$ and $R^8$ form a phthaloyl group.

$R^9$ represents a hydrogen atom, a p-toluenesulfonyl group or a benzyl group, $R^{10}$ represents a hydrogen atom or a p-toluenesulfonyl group, $R^{11}$ represents a hydrogen atom, an ethyl group, an aldehyde group, a cyclopropylmethyl group or a group represented by the following Formula (IV), or $R^{10}$ and $R^{11}$ form a phthaloyl group.

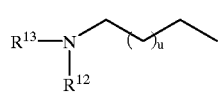

(IV)

In Formula (IV), u is 1 or 2, $R^{12}$ represents a hydrogen atom or a p-toluenesulfonyl group, $R^{13}$ represents a hydrogen atom, an ethyl group, or a cyclopropylmethyl group.

The present invention also relates to anticancer agents containing, as an active ingredient, at least one of the compounds represented by the above Formula (I) or (III) and/or pharmaceutically acceptable salts thereof. More specifically, the present invention relates to anticancer agents containing, as an active ingredient, at least one of 1,18-bis(ethylamino)-5,14-diazaoctadecane (Formula (V)), 1,16-bis(cyclopropylmethylamino)-5,12-diazahexadecane (Formula (VI)), 1,17-bis(cyclopropylmethylamino)-5,13-diazaheptadecane (Formula (VII)) and/or pharmaceutically acceptable salts thereof.

DETAILED DESCRIPTION OF PREFERRED EMBODIMENTS

Novel Polyamine Compounds

Figure 1:
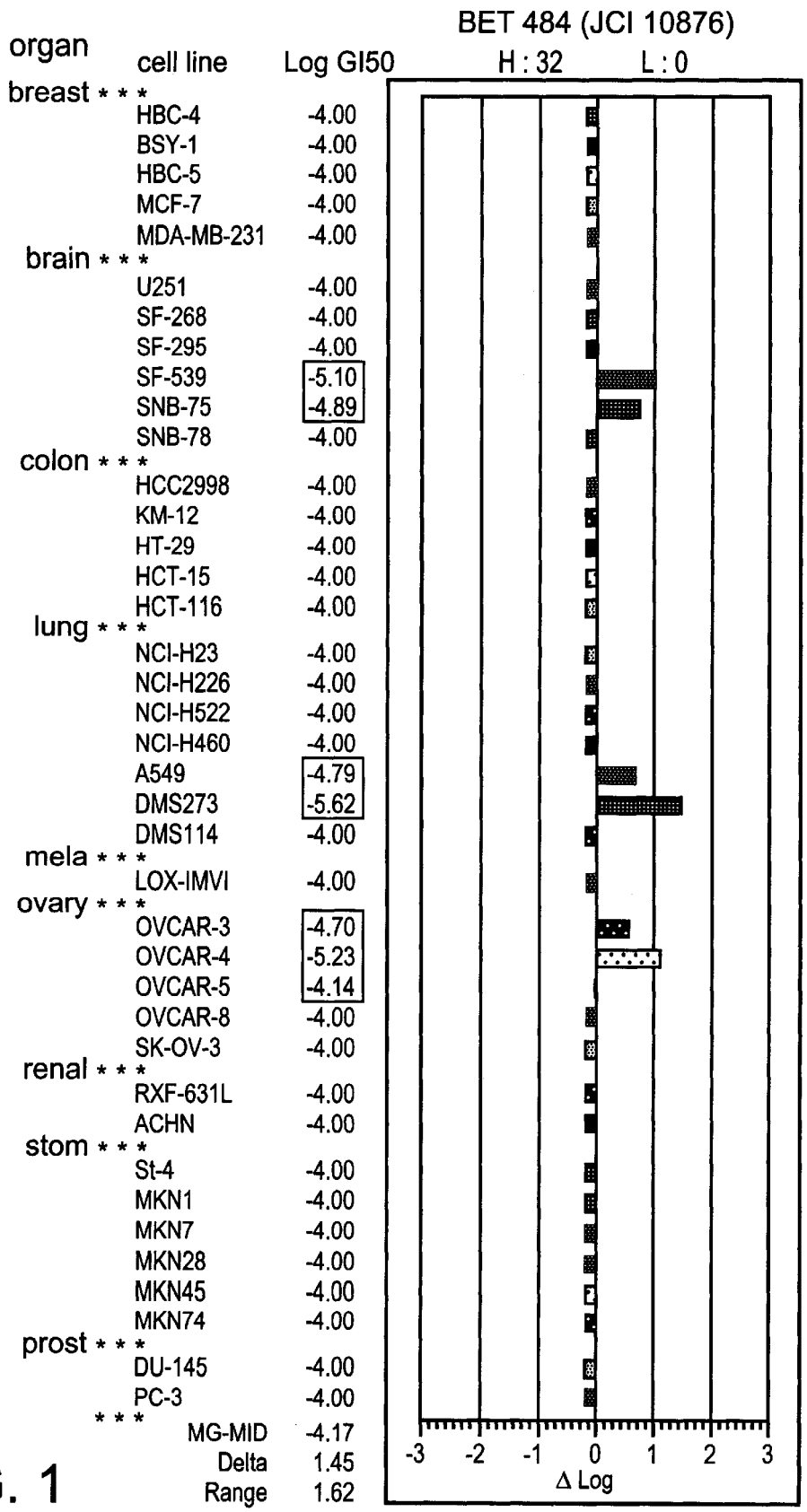
FIG. 1 is a mean graph obtained in the carcinostatic effect screening in Example 14 (BET484).
Figure 2:
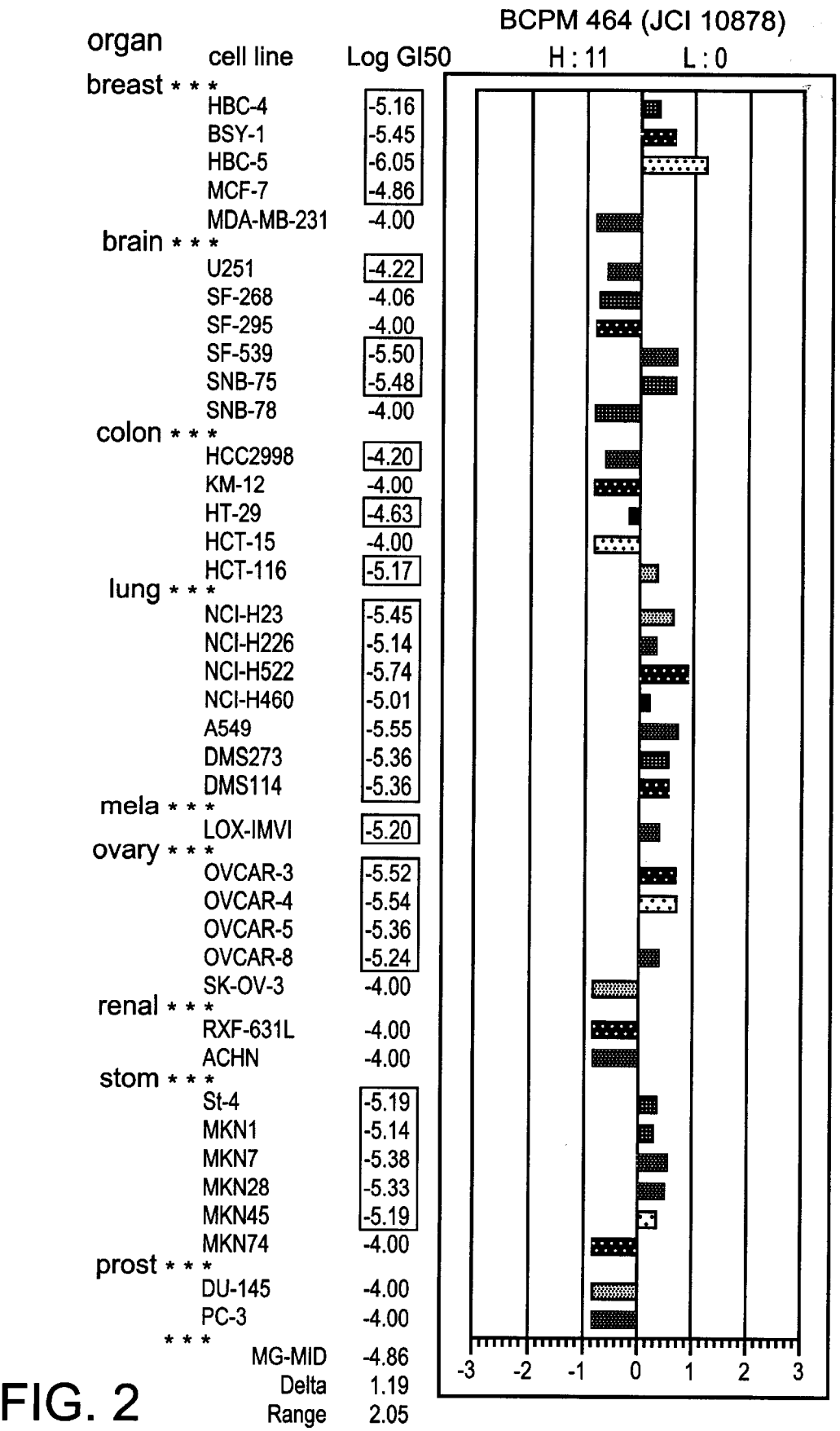
FIG. 2 is a mean graph obtained in the carcinostatic effect screening in Example 14 (BCPM464).
Figure 3:
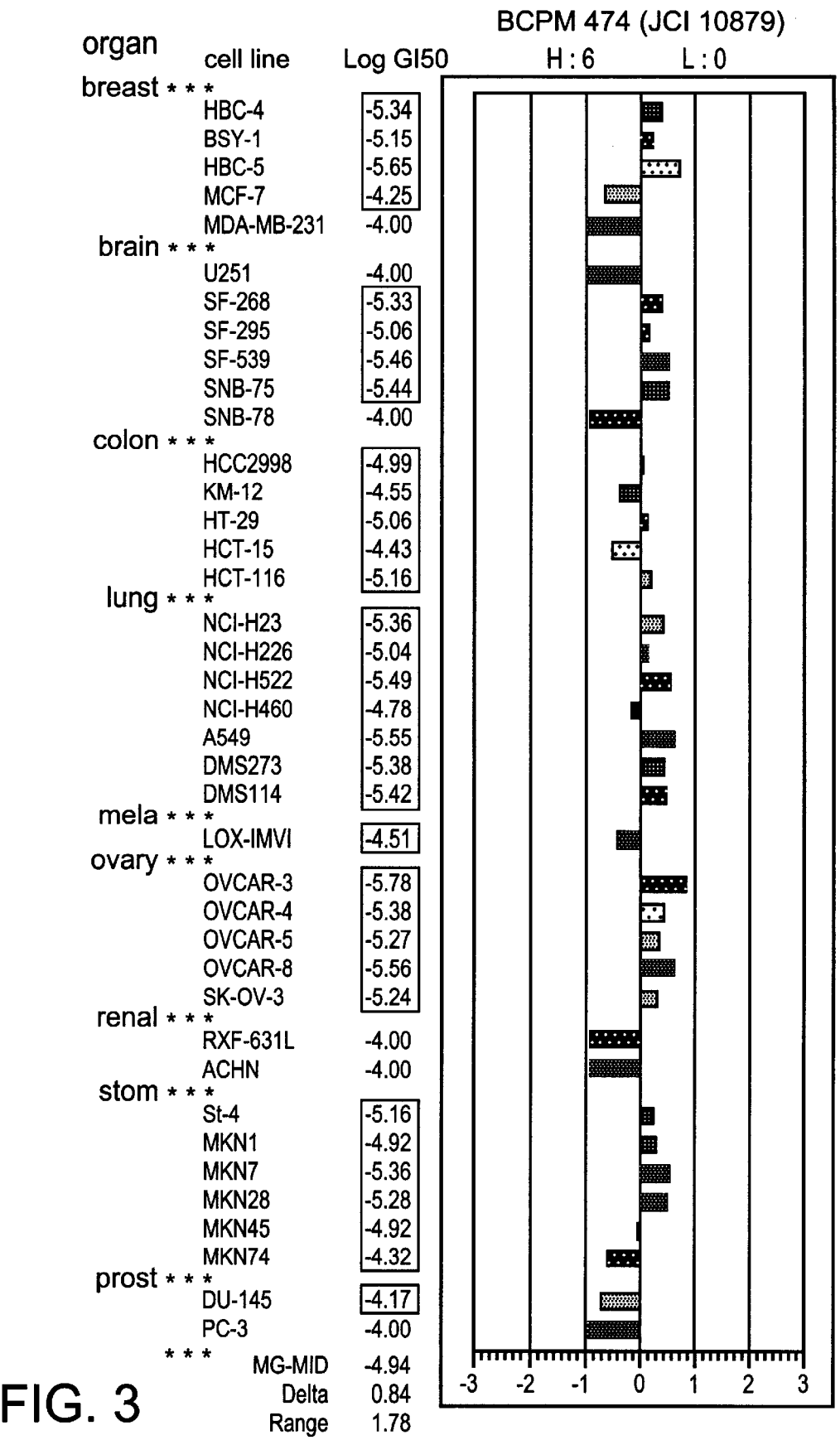
FIG. 3 is a mean graph obtained in the carcinostatic effect screening in Example 14 (BCPM474).

Among Compounds 1 to 54a and b described in the examples mentioned below (except for Compounds 22, 27, 32 and 37), Compounds 1 to 5, 11 to 17, 20, 21, 42 to 44, 48 and 49 are represented by the Formula (I). Compounds 6 to 10, 18, 19, 22 to 41 and 45 to 47 are represented by the Formula (III). The following tables list relationships between each compound and Formula (I) or (III). In the tables, Et, Ts, CPM and Phth represent ethyl group, p-toluenesulfonyl group, cyclopropylmethyl group and phthaloyl group, respectively.

TABLE 1

Groups and values of integers in compounds represented by Formula (I)

| Compound | $R^1$ | $R^2$ | $R^3$ | $R^4$ | $R^5$ | $R^6$ | n | m |
|---|---|---|---|---|---|---|---|---|
| 1 | Ts | Formula (II) | Ts | Formula (II) | Phth | Phth | 2 | 1 |
| 2 | Ts | Formula (II) | Ts | Formula (II) | H | CHO | 2 | 1 |
| 3 | Ts | Formula (II) | Ts | Formula (II) | Ts | H | 2 | 1 |
| 4 | Ts | Formula (II) | Ts | Formula (II) | Ts | Et | 2 | 1 |
| 5 | H | Formula (II) | H | Formula (II) | H | Et | 2 | 1 |
| 11a–h | Ts | Formula (II) | Ts | Formula (II) | Phth | Phth | a:1<br>b:2<br>c:3<br>d:4<br>e:5<br>f:6<br>g:7<br>h:8 | 2 |
| 12a–h | Ts | Formula (II) | Ts | Formula (II) | H | CHO | a:1<br>b:2 | 2 |

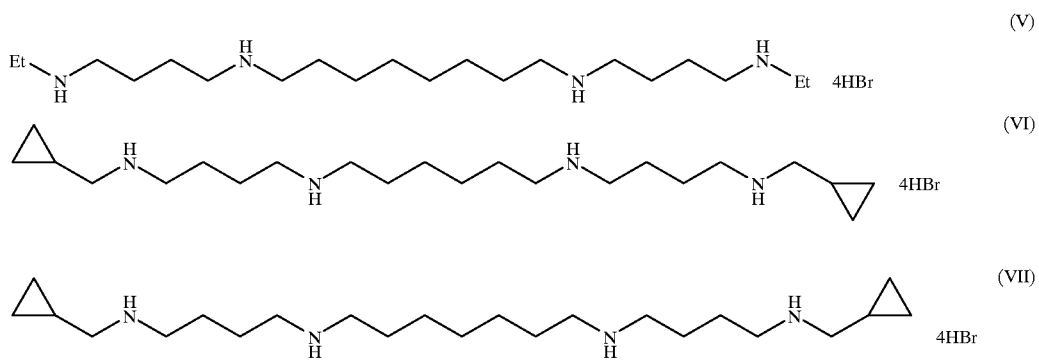

TABLE 1-continued

Groups and values of integers in compounds represented by Formula (I)

| Compound | R¹ | R² | R³ | R⁴ | R⁵ | R⁶ | n | m |
|---|---|---|---|---|---|---|---|---|
| | | | | | | | c:3 | |
| | | | | | | | d:4 | |
| | | | | | | | e:5 | |
| | | | | | | | f:6 | |
| | | | | | | | g:7 | |
| | | | | | | | h:8 | |
| 13a–h | Ts | Formula (II) | Ts | Formula (II) | Ts | H | a:1 | 2 |
| | | | | | | | b:2 | |
| | | | | | | | c:3 | |
| | | | | | | | d:4 | |
| | | | | | | | e:5 | |
| | | | | | | | f:6 | |
| | | | | | | | g:7 | |
| | | | | | | | h:8 | |
| 14a–h | Ts | Formula (II) | Ts | Formula (II) | Ts | Et | a:1 | 2 |
| | | | | | | | b:2 | |
| | | | | | | | c:3 | |
| | | | | | | | d:4 | |
| | | | | | | | e:5 | |
| | | | | | | | f:6 | |
| | | | | | | | g:7 | |
| | | | | | | | h:8 | |

TABLE 2

Groups and values of integers in compounds represented by Formula (I)

| Compound | R¹ | R² | R³ | R⁴ | R⁵ | R⁶ | n | m |
|---|---|---|---|---|---|---|---|---|
| 15a–h | H | Formula (II) | H | Formula (II) | H | Et | a:1 | 2 |
| | | | | | | | b:2 | |
| | | | | | | | c:3 | |
| | | | | | | | d:4 | |
| | | | | | | | e:5 | |
| | | | | | | | f:6 | |
| | | | | | | | g:7 | |
| | | | | | | | h:8 | |
| 16 | Ts | Formula (II) | Ts | Formula (II) | Ts | CPM | 2 | 1 |
| 17 | H | Formula (II) | H | Formula (II) | H | CPM | 2 | 1 |
| 20a–h | Ts | Formula (II) | Ts | Formula (II) | Ts | CPM | a:1 | 2 |
| | | | | | | | b:2 | |
| | | | | | | | c:3 | |
| | | | | | | | d:4 | |
| | | | | | | | e:5 | |
| | | | | | | | f:6 | |
| | | | | | | | g:7 | |
| | | | | | | | h:8 | |
| 21a–h | H | Formula (II) | H | Formula (II) | H | CPM | a:1 | 2 |
| | | | | | | | b:2 | |
| | | | | | | | c:3 | |
| | | | | | | | d:4 | |
| | | | | | | | e:5 | |
| | | | | | | | f:6 | |
| | | | | | | | g:7 | |
| | | | | | | | h:8 | |
| 42 | H | Formula (II) | H | Formula (II) | H | H | 1 | 2 |
| 43 | H | Formula (II) | H | Formula (II) | H | H | 6 | 2 |
| 44 | H | Formula (II) | H | Formula (II) | H | H | 8 | 2 |
| 48a | Ts | Et | Ts | Et | — | — | 6 | — |
| 48b | H | Et | H | Et | — | — | 6 | — |
| 49a | Ts | Et | Ts | Et | — | — | 3 | — |
| 49b | H | Et | H | Et | — | — | 3 | — |

TABLE 3

Groups and values of integers in compounds represented by Formula (III)

| Compound | R⁷ | R⁸ | R⁹ | R¹⁰ | R¹¹ | R¹² | R¹³ | p | q | u |
|---|---|---|---|---|---|---|---|---|---|---|
| 6 | Phth | Phth | Ts | Phth | Phth | — | — | 1 | 2 | — |
| 7 | H | CHO | Ts | H | CHO | — | — | 1 | 2 | — |
| 8 | Ts | H | Ts | Ts | H | — | — | 1 | 2 | — |
| 9 | Ts | Et | Ts | Ts | Et | — | — | 1 | 2 | — |
| 10 | H | Et | H | H | Et | — | — | 1 | 2 | — |
| 18 | Ts | CPM | Ts | Ts | CPM | — | — | 1 | 2 | — |
| 19 | H | CPM | H | H | CPM | — | — | 1 | 2 | — |
| 23 | Ts | Et | Ts | H | CHO | — | — | 1 | 2 | — |
| 24 | Ts | CPM | Ts | H | CHO | — | — | 1 | 2 | — |
| 25 | H | Et | H | H | H | — | — | 1 | 2 | — |
| 26 | H | CPM | H | H | H | — | — | 1 | 2 | — |
| 28 | Ts | Et | Bn | Ts | Et | — | — | 1 | 1 | — |
| 29 | Ts | CPM | Bn | Ts | CPM | — | — | 1 | 1 | — |
| 30 | H | Et | Bn | H | Et | — | — | 1 | 1 | — |
| 31 | H | CPM | Bn | H | CPM | — | — | 1 | 1 | — |
| 33 | Ts | Formula (IV) | Bn | Ts | Formula (IV) | Ts | Et | 1 | 1 | 1 |
| 34 | Ts | Formula (IV) | Bn | Ts | Formula (IV) | Ts | CPM | 1 | 1 | 1 |
| 35 | H | Formula (IV) | Bn | H | Formula (IV) | H | Et | 1 | 1 | 1 |
| 36 | H | Formula (IV) | Bn | H | Formula (IV) | H | CPM | 1 | 1 | 1 |
| 38 | Ts | Formula (IV) | Bn | Ts | Formula (IV) | Ts | Et | 1 | 1 | 2 |
| 39 | Ts | Formula (IV) | Bn | Ts | Formula (IV) | Ts | CPM | 1 | 1 | 2 |
| 40 | H | Formula (IV) | Bn | H | Formula (IV) | H | Et | 1 | 1 | 2 |
| 41 | H | Formula (IV) | Bn | H | Formula (IV) | H | CPM | 1 | 1 | 2 |
| 45 | H | H | Bn | H | H | — | — | 1 | 1 | — |
| 46 | H | Formula (IV) | Bn | H | Formula (IV) | H | H | 1 | 1 | 1 |
| 47 | H | Formula (IV) | Bn | H | Formula (IV) | H | H | 1 | 1 | 2 |

Pharmaceutically acceptable salts may be inorganic or organic acid salts. Inorganic acid salts include, but are not limited to, hydrochlorides, bromates and so forth. Organic acid salts include, but are not limited to, acetates, citrates and so forth. Among these, bromates are preferred.

The novel polyamine compounds of the present invention are water-soluble linear polyamine derivatives that can be systematically synthesized starting form a simple linear polyamine by systematically extending its both ends symmetrically or asymmetrically, and then introducing an ethyl substituent or a cyclopropylmethyl substituent into primary amino groups at the both ends of the linear polyamines.

Specifically, an alkanediamine such as diaminobutane, diaminopropane, diaminopentane, diaminohexane, diaminoheptane, diaminooctane, diaminononane and diaminodecane is reacted with tosyl chloride at room temperature for 1 to 3 hours. The obtained Na,Nw-di(p-toluenesulfonyl)-a,w-diaminoalkane (a and w represent integers corresponding to each diaminoalkane used, this compound is referred to as Chain A hereinafter) is used as a starting material. Alkyl chains (referred to as Chain B hereinafter) having such a structure that both ends of the diaminoalkane should be converted into primary amino groups when reacted with the above Chain A are introduced into Chain A. More specifically, for example, by using a haloalkane in which one end of alkyl chain is bound to a phthalimide group or a tosylamide group as Chain B, it is possible to convert one end of chain B into a primary amino group. Specifically, in order to introduce the obtained Chain B into Chain A, for example, Chain A and Chain B can be reacted at a temperature from room temperature to 80° C. for several hours to 3days in the presence of a base. The obtained compound corresponds to Compound 1 in Scheme 1, Compound 6 in Scheme 2 and Compound 11 in Scheme 3.

The compound obtained by introducing Chain B into Chain A is converted into a corresponding tosylamide derivative by known methods (Patent Documents 1 to 5 and References 6 to 8). Specifically, the obtained compound is reacted with $N_2H_4$ in DMF at 60 to 80° C. for 1 day. This reaction corresponds to Process a in Schemes 1 to 3 described below. The obtained compound is reacted at 40 to 80° C. for 1 to 3 hours in 2 N HCl, then reacted with TsCl at room temperature for 3 to 4 hours in the presence of pyridine and $NEt_3$ to obtain a tosylamide derivative (Compound 3 in Scheme 1, Compound 8 in Scheme 2 and Compound 13 in Scheme 3). This reaction corresponds to Process b in Schemes 1 to 3 described below.

Starting from the tosylamide derivative obtained by the above method, an alkyl group such as ethyl group and cyclopropylmethyl group is systematically introduced into the tosylamide derivative by the methods described in References 1 to 8 to synthesize a polyamine compound. Specifically, in order to introduce ethyl group into a tosylamide derivative, the tosylamide derivative is reacted with Et-Br at room temperature for 3 days in DMF containing $K_2CO_3$. This reaction corresponds to Process c in Schemes 1 to 3 and 12 and Process a in Schemes 7 to 10. On the other hand, a cyclopropylmethyl group can be introduced into the tosylamide derivative by allowing the tosylamide derivative to react with cyclopropylmethyl at room temperature for 3 days in DMF containing $K_2CO_3$. This reaction corresponds to Process a in Schemes 4 to 6 and Process b in Schemes 7 to 10.

The obtained compound introduced with ethyl group or cyclopropylmethyl group is then detosylated. Detosylation can be performed by the methods described in References 6 to 8. Specifically, for example, a detosylated compound can be obtained by treating the compound introduced with ethyl group or cyclopropylmethyl group with 33% HBr in AcOH (acetic acid). This reaction corresponds to Process a in Schemes 1 to 3 and 12, Process b in Schemes 4 to 6, Process c in Schemes 7 to 10, and Process a in Scheme 11.

The following are a list of references.
1) Iwata, Yamamoto and Nakajima, Japanese Patent Laid-open No. 08-027129 (Publication Date: Jan. 30, 1996), "Cyclic polyamine and antiviral agent containing the same as active ingredient"
2) Iwata and Kuzuhara, Japanese Patent No. 1857707, "Method for producing N-alkylformamide"
3) Iwata and Kuzuhara, Japanese Patent No. 1857749, "Polyamine derivative"
4) Iwata and Kuzuhara, Japanese Patent No. 1998558, "Method for producing polyamine derivatives"
5) Iwata and Kuzuhara, Japanese Patent No. 2123326 "N-phthalimide derivative and method for producing the same"
6) M. Iwata and H. Kuzuhara, Synth. Commun., 19, pp.1009–1014 (1989)
7) M. Iwata and H. Kuzuhara, Bull. Chem. Soc. Jpn., 62, pp.198–210 (1989)
8) M. Iwata and H. Kuzuhara, Bull. Chem. Soc. Jpn., 62, pp.1102–1106 (1989)

Anticancer Agents Containing Polyamine Compounds

The anticancer agents of the present invention contain at least one of the compounds represented by the above Formula (I) or (III) and/or pharmaceutically acceptable salts thereof as an active ingredient. More specifically, the anticancer agents include those containing as an active ingredient at least one of 1,18-bis(ethylamino)-5,14-diazaoctadecane (a compound of the present invention represented by Formula (I), Compound 15f in Scheme 3 mentioned below), 1,16-bis(cyclopropylmethylamino)-5,12-diazahexadecane (a compound of the present invention represented by Formula (I), Compound 21d in Scheme 6 mentioned below), 1,17-bis(cyclopropylmethylamino)-5,13-diazaheptadecane (a compound represented by Formula (I) of the present invention, Compound 21e in Scheme 6 mentioned below) and/or pharmaceutically acceptable salts thereof.

The pharmaceutically acceptable salts may be either inorganic acid salts or organic acid salts. Inorganic acid salts include, but are not limited to, hydrochlorides, bromates and so on. Organic acid salts include, but are not limited to, acetates, citrates and so on. Among these, bromates can preferably be used.

The anticancer agents of the present invention contain, for example, 0.1 µg to 1000 mg of the above compounds and/or pharmaceutically acceptable salts thereof as an active ingredient. These can be administered at one to three times a day, for example. The anticancer agents of the present invention can be administered orally, intravenously, intramuscularly, subcutaneously, intraperitoneally, or via other routes, and used in a form suitable for each administration route. Dosages are suitably determined considering species, body weight, age, physical conditions of individuals, dosage form and so forth.

The anticancer agents of the present invention can be in the form of any one of usual pharmaceutical preparations, for example, tablet, coated tablet, capsule, powder, granule, aqueous solution such as isotonic solution, aqueous or oily suspension, syrup, decoction, drop or the like. The anticancer agents of the present invention can contain usual adjuvants, excipients and additives.

EXAMPLES

Example 1

Synthesis of 1,12-di(ethylamino)-4,9-diazadodecane HBr Salt (5) (Scheme 1)

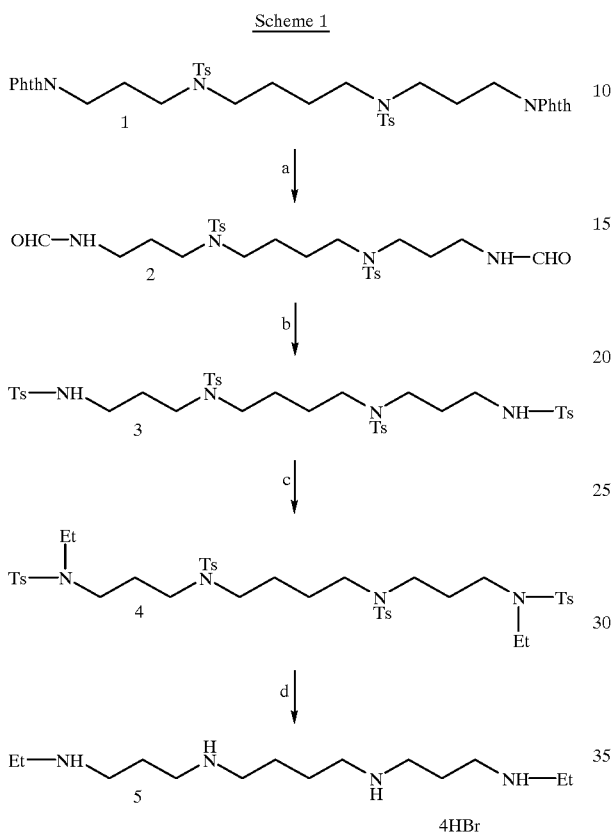

a N₂H₄/DMF 70° C. 1d, b; 1. 2N—HCl 70° C. 1h, 2. TsCl/Py/NEt₃ rt 4h, c Et—Br/K₂CO₃/DMF d 33%-HBr—AcOH

[ Phth = phthaloyl,
Ts = p-toluenesulfonyl,
Et = ethyl,
DMF = N,N-dimethylformamide,
AcOH = acetic acid ]

Diaminobutane as a raw material was reacted with tosyl chloride at room temperature for 3 hours to obtain N1,N4-di(p-toluenesulfonyl)-1,4-diaminobutane. Using the obtained N1,N4 -di (p-toluenesulfonyl)-1,4-diaminobutane and N-(3-bromopropyl)phthalimide as Chain A and Chain B, respectively, N1,N4,N9,N12-tetra(p-toluenesulfonyl)-1,12-diamino-4,9-diaz adodecane (3) was derived from the above Chain A and Chain B according to the known methods (Patent Documents 1 to 5 and References 6 to 8). Specifically, Compound 1 was synthesized, and then this Compound 1 was reacted with N₂H₄ in DMF at 70° C. for 1 day to obtain Compound 2. The obtained Compound 2 was first treated with 2N HCl at 70° C. for 1 hour, and then reacted with TsCl in pyridine (Py) in the presence of NEt₃ at room temperature for 4 hours to obtain Compound 3.

Subsequently, a mixture of the above Compound 3 (0.17 g), anhydrous potassium carbonate (0.143 g) and bromoethane (57 mg) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N4,N9,N12-tetra(p-toluenesulfonyl)-1,12-di(ethylamino)-4,9-diazadodecane (4, 0.106 g, yield: 58%). The results of elementary analysis of Compound 4 are shown in Table 4 below, and the results of ¹H-NMR and ¹³C-NMR of the same are shown Table 8 below, respectively. The obtained Compound 4 (96mg) was heated with phenol (0.206 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became color less. The solvent was evaporated under reduced pressure to obtain Compound5 (see Scheme 1) as colorless powder.

Example 2

Synthesis of 1,8-di(ethylamino)-4-azaoctane HBr Salt (10) (Scheme 2)

a N₂H₄/DMF 70° C. 1d, b; 1. 2N—HCl 70° C. 1h, 2. TsCl/Py/NEt₃ rt 4h, c Et—Br/K₂CO₃/DMF d 33%-HBr—AcOH

3 -Bromopropylamine as a raw material was reacted with tosyl chloride at 0° C. for 2 hours to synthesize N-(p-toluenesulfonyl)-3-bromopropylamine. Further, this was reacted with phthalimide at room temperature for 3 days to obtain N-(N3-p-toluenesulfonyl-3-aminopropyl) phthalimide. Using the obtained N-(N3-p-toluenesulfonyl-3-aminopropyl)phthalimide and N-(4-bromobutyl) phthalimide as Chain A and Chain B, respectively, N1,N4,N8-tri(p-toluenesulfonyl)-1,8-diamino-4-azaoctane (8) was derived from the above Chain A and Chain B according to the known methods (Patent Documents 1 to 5 and References 6 to 8). Specifically, Compound 6 was synthesized, and then this Compound 6 was reacted with $N_2H_4$ in DMF at 70° C. for 1 day to obtain Compound 7. The obtained Compound 7 was first treated with 2 N HCl at 70° C. for 1 hour, and then reacted with TsCl in pyridine in the presence of $NEt_3$ at room temperature for 4 hours to obtain Compound 8.

Subsequently, a mixture of the above Compound 8 (0.157 g), anhydrous potassium carbonate (0.178 g) and bromoethane (48 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N4,N8-tri(p-toluenesulfonyl)-1,8-di(ethylamino)-4-azaoct ane (9, 0. 111 g, yield: 65%). The results of elementary analysis of Compound 9 are shown in Table 1 below, and the results of $^1$H-NMR and $^{13}$C-NMR of the same are shown in Table 8 below, respectively. The obtained Compound 9 (100 mg) was heated with phenol (0.283 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 10 (see Scheme 2) as colorless powder.

Example 3.1

Synthesis of 1,13-di(ethylamino)-5,9-diazatridecane HBr Salt (15a) (Scheme 3)

Scheme 3

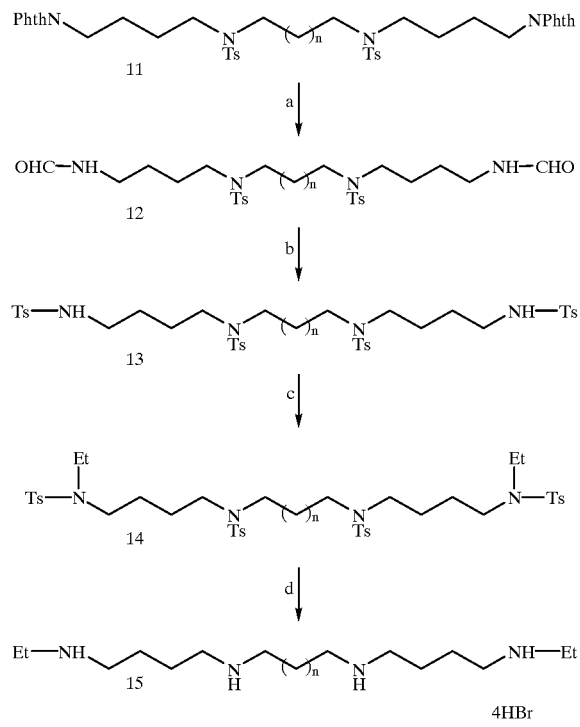

-continued
a $N_2H_4$/DMF 70° C. 1d, b; 1. 2N-HCl 70° C. 1h, 2. TsCl/Py/NEt$_3$ rt 4h, c Et-Br/K$_2$CO$_3$/DMF d 33%-HBr-AcOH $$\begin{bmatrix} a\,n=1, b\,n=2, c\,n=3, \\ d\,n=4, e\,n=5, f\,n=6, \\ g\,n=7, h\,n=8 \end{bmatrix}$$

Diaminopropane as a raw material was reacted with tosyl chloride at room temperature for 3 hours to obtain N1,N3-di(p-toluenesulfonyl)-1,3-diaminopropane. Using the obtained N1,N3-di(p-toluenesulfonyl)-1,3-diaminopropane and N-(4-bromobutyl) phthalimideas Chain A and Chain B, respectively, N1,N5,N9,N13-tetra(p-toluenesulfonyl)-1,13-diamino-5,9-diaz atridecane (13a) was derived from the above Chain A and Chain B according to the known methods (Patent Documents 1 to 5 and References 6to 8). Specifically, Compound 11a was synthesized, and then this Compound 11a was reacted with $N_2H_4$ in DMF at 70° C. for 1 day to obtain Compound 12a. The obtained Compound 12a was first treated with 2 NHCl at 70° C. for 1 hour, and then reacted with TsCl in pyridine in the presence of $NEt_3$ at room temperature for 4 hours to obtain Compound 13a.

Then, a mixture of the above Compound 13a (0.229 g), anhydrous potassium carbonate (0.190 g) and bromoethane (51 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N9,N13-tetra(p-toluenesulfonyl)-1,13-di(ethylamino)-5,9-diazatridecane (14a, 0.215 g, yield: 88%). The results of elementary analysis of Compound 14a are shown in Table 4 below, and the results of $^1$H-NMR and $^{13}$C-NMR of the same are shown in Table 8 below, respectively. The obtained Compound 14a (202 mg) was heated with phenol (0.428 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15a (see Scheme 3) as colorless powder.

Example 3.2

Synthesis of 1,14-di(ethylamino)-5,10-diazatetradecane HBr Salt (15b) (Scheme 3)

Diaminobutane as a raw material was reacted with tosyl chloride at room temperature for 3 hours to obtain N1,N4-di(p-toluenesulfonyl)-1,4-diaminobutane. Using the obtained N1,N4-di(p-toluenesulfonyl)-1,4-diaminobutane and N-(4-bromobutyl)phthalimide as Chain A and Chain B, respectively, N1,N5,N10,N14-tetra(p-toluenesulfonyl)-1, 14-diamino-5,10-di azatetradecane (13b) was derived from the above Chain A and Chain B according to the known methods (Patent Documents 1 to 5 and References 6 to 8). Specifically, Compound 11b was synthesized, and then this Compound 11b was reacted with $N_2H_4$ in DMF at 70° C. for 1 day to obtain Compound 12b. The obtained Compound 12b was first treated with 2 N HCl at70° C. for hour, and then reacted with TsCl in pyridine in the presence of $NEt_3$ at room temperature for 4 hours to obtain Compound 13b.

Subsequently, a mixture of the above Compound 13b (0.179 g), anhydrous potassium carbonate (0.146 g) and bromoethane (40 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N10,N14-tetra(p-toluenesulfonyl)-1,14-di(ethylamino)-5,10-diazatetradecane (14b, 0.215 g, yield: 88%). The results of elementary analysis of Compound 14b are shown in Table 4 below, and the results of $^1$H-NMR and $^{13}$C-NMR of the same are shown in Table 8 below, respectively. The obtained Compound 14b (114 mg) was heated with phenol (0.238 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15b (see Scheme 3) as colorless powder.

Example 3.3

Synthesis of 1,15-di(ethylamino)-5,11-diazapentadecane HBr Salt (15c) (Scheme 3)

Diaminopentane as a raw material was reacted with tosyl chloride to obtain N1,N5-di(p-toluenesulfonyl)-1,5-diaminopentane. Using the obtained N1,N5-di(p-toluenesulfonyl)-1,5-diaminopentane and N-(4-bromobutyl)phthalimide as Chain A and Chain B, respectively, N1,N5,N11,N15-tetra(p-toluenesulfonyl)-1,15-diamino-5,11-di azapentadecane (13c) was derived from the above Chain A and Chain B according to the known methods (Patent Documents 1 to 5 and References 6 to 8). Specifically, Compound 11c was synthesized, and then this Compound 11c was reacted with N$_2$H$_4$ in DMF at 70° C. for 1 day to obtain Compound 12c. The obtained Compound 12c was first treated with 2 N HCl at 70° C. for 1 hour, and then reacted with TsCl in pyridine in the presence of NEt$_3$ at room temperature for 4 hours to obtain Compound 13c.

Subsequently, a mixture of the above Compound 13c (0.186 g), anhydrous potassium carbonate (0.149 g) and bromoethane (40 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N11,N15-tetra(p-toluenesulfonyl)-1,15-di(ethylamino)-5,11-diazapentadecane (14c, 0.173 g, yield: 87%). The results of elementary analysis of Compound 14c are shown in Table 4 below, and the results of $^1$H-NMR and $^{13}$C-NMR of the same are shown in Table 8 below, respectively. The obtained Compound 14c (163 mg) was heated with phenol (0.334 g) in 33% HBr in acetic acid (13 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15c (see Scheme 3) as colorless powder.

Example 3.4

Synthesis of 1,16-di(ethylamino)-5,12-diazahexadecane HBr Salt (15d) (Scheme 3)

Diaminohexane as a raw material was reacted with tosyl chloride to obtain N1,N6-di(p-toluenesulfonyl)-1,6-diaminohexane. Using the obtained N1,N6-di(p-toluenesulfonyl)-1,6-diaminohexane and N-(4-bromobutyl)phthalimide as Chain A and Chain B, respectively, N1,N5,N12,N16-tetra(p-toluenesulfonyl)-1,16-diamino-5,12-di azahexadecane (13d) was derived from the above Chain A and Chain B according to the known methods (Patent Documents 1 to 5 and References 6 to 8). Specifically, Compound 11d was synthesized, and then this Compound 11d was reacted with N$_2$H$_4$ in DMF at 70° C. for 1 day to obtain Compound 12d. The obtained Compound 12d was first treated with 2 N HCl at 70° C. for 1 hour, and then reacted with TsCl in pyridine in the presence of NEt$_3$ at room temperature for 4 hours to obtain Compound 13d.

Subsequently, a mixture of the above Compound 13d (0.208 g), anhydrous potassium carbonate (0.164 g) and bromoethane (44 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N12,N16-tetra(p-toluenesulfonyl)-1,16-di(ethylamino)-5,12-diazahexadecane (14d, 0.243 g, yield: 99%). The results of elementary analysis of Compound 14d are shown in Table 4 below, and the results of $^1$H-NMR and $^{13}$C-NMR of the same are shown in Table 8 below, respectively. The obtained Compound 14d (233 mg) was heated with phenol (0.471 g) in 33% HBr in acetic acid (13 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15d (see Scheme 3) as colorless powder.

Example 3.5

Synthesis of 1,17-di(ethylamino)-5,13-diazaheptadecane HBr Salt (15e) (Scheme 3)

Diaminoheptane as a raw material was reacted with tosyl chloride at room temperature for 3 hours to obtain N1,N7-di(p-toluenesulfonyl)-1,7-diaminoheptane. Using the obtained N1,N7-di(p-toluenesulfonyl)-1,7-diaminoheptane and N-(4-bromobutyl)phthalimide as Chain A and Chain B, respectively, N1,N5, N13, N17-tetra(p-toluenesulfonyl)-1,17-diamino-5,13-di azaheptadecane (13e) was derived from the above Chain A and Chain B according to the known methods (Patent Documents 1 to 5 and References 6 to 8). Specifically, Compound 11e was synthesized, and then this Compound 11e was reacted with N$_2$H$_4$ in DMF at 70° C. for 1 day to obtain Compound 12e. The obtained Compound 12e was first treated with 2N HCl at 70° C. for 1 hour, and then reacted with TsCl in pyridine in the presence of NEt$_3$ at room temperature for 4 hours to obtain Compound 13e.

Subsequently, a mixture of the above Compound 13e (0.160 g), anhydrous potassium carbonate (0.180 g) and bromoethane (38 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N13,N17-tetra(p-toluenesulfonyl)-1,17-di(ethylamino)-5,13-diazaheptadecane (14e, 0.152 g, yield: 89%). The results of elementary analysis of Compound 14e are shown in Table 4 below, and the results of $^1$H-NMR and $^{13}$C-NMR of the same are shown in Table 9 below, respectively. The obtained Compound 14e (142 mg) was heated with phenol (0.283 g) in 33% HBr in acetic acid (13 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15e (see Scheme 3) as colorless powder.

Example 3.6

Synthesis of 1,18-di(ethylamino)-5,14-diazaoctadecane HBr Salt (15f) (Scheme 3)

Diaminooctane as a raw material was reacted with tosyl chloride at room temperature for 3 hours to obtain N1,N8-di(p-toluenesulfonyl)-1,8-diaminooctane. Using the obtained N1,N8-di(p-toluenesulfonyl)-1,8-diaminooctane and N-(4-bromobutyl)phthalimide as Chain A and Chain B, respectively, N1,N5,N14,N18-tetra(p-toluenesulfonyl)-1,18-diamino-5,14-di azaoctadecane (13f) was derived from the above Chain A and Chain B according to the known methods (Patent Documents 1 to 5 and References 6 to 8). Specifically, Compound 11f was synthesized, and then this Compound 11 f was reacted with N$_2$H$_4$ in DMF at 70° C. for 1 day to obtain Compound 12f. The obtained Compound 12f was first treated with 2 N HCl at 70° C. for 1 hour, and then reacted with TsCl in pyridine in the presence of NEt$_3$ at room temperature for 4 hours to obtain Compound 13f.

Subsequently, a mixture of the above Compound 13f (0.177 g), anhydrous potassium carbonate (0.135 g) and bromoethane (37 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N14,N18-tetra(p-toluenesulfonyl)-1,18-di(ethylamino)-5,14-diazaoctadecane (14f, 0.173 g, yield: 92%). The results of elementary analysis of Compound 14f are shown in Table 4 below, and the results of $^1$H-NMR and $^{13}$C-NMR of the same are shown in Table 9 below, respectively. The obtained Compound 14f (163 mg) was heated with phenol (0.320 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15f (see Scheme 3) as colorless powder.

Example 3.7

Synthesis of 1,19-di(ethylamino)-5,15-diazanonadecane HBr Salt (15g) (Scheme 3)

Diaminononane as a raw material was reacted with tosyl chloride at room temperature for 3 hours to obtain N1,N9-di(p-toluenesulfonyl)-1,9-diaminononane. Using the obtained N1,N9-di(p-toluenesulfonyl)-1,9-diaminononane and N-(4-bromobutyl)phthalimide as Chain A and Chain B, respectively, N1,N5,N15,N19-tetra(p-toluenesulfonyl)-1,19-diamino-5,15-di azanonadecane (13 g) was derived from the above Chain A and Chain B according to the known methods (Patent Documents 1 to 5 and References 6 to 8). Specifically, Compound 11g was synthesized, and then this Compound 11g was reacted with N$_2$H$_4$ in DMF at 70° C. for 1 day to obtain Compound 12g. The obtained Compound 12g was first treated with 2 N HCl at 70° C. for 1 hour, and then reacted with TsCl in pyridine in the presence of NEt$_3$ at room temperature for 4 hours to obtain Compound 13g.

Subsequently, a mixture of the above Compound 13g (0.168 g), anhydrous potassium carbonate (0.126 g) and bromoethane (34 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N15,N19-tetra(p-toluenesulfonyl)-1,19-di(ethylamino)-5,15-diazanonadecane (14 g, 0.174 g, yield: 98%). The results of elementary analysis of Compound 14 g are shown in Table 4 below, and the results of $^1$H-NMR and $^{13}$C-NMR of the same are shown in Table 9 below, respectively. The obtained Compound 14 g (164 mg) was heated with phenol (0.320 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15 g (see Scheme 3) as colorless powder.

Example 3.8

Synthesis of 1,20-di(ethylamino)-5,16-diazaeicosane HBr Salt (15h) (Scheme 3)

Diaminodecane as a raw material was reacted with tosyl chloride at room temperature for 3 hours to obtain N1,N10-di(p-toluenesulfonyl)-1,10-diaminodecane. Using the obtained N1,N10-di(p-toluenesulfonyl)-1,10-diaminodecane and N-(4-bromobutyl)phthalimide as Chain A and Chain B, respectively, N1,N5,N16,N20-tetra(p-toluenesulfonyl)-1,20-diamino-5,16-di azaeicosane (13h) was derived from the above Chain A and Chain B according to the known methods (Patent Documents 1 to 5 and References 6 to 8). Specifically, Compound 11h was synthesized, and then this Compound 11h was reacted with N$_2$H$_4$ in DMF at 70° C. for 1 day to obtain Compound 12h. The obtained Compound 12h was first treated with 2 N HCl at 70° C. for 1 hour, and then reacted with TsCl in pyridine in the presence of NEt$_3$ at room temperature for 4 hours to obtain Compound 13h.

Subsequently, a mixture of the above Compound 13h (0.170 g), anhydrous potassium carbonate (0.126 g) and bromoethane (34 ml) was allowed to react in DMF (40 ml) at room temperature for 3 days with stirring, filtered, and then concentrated. A substance exhibiting Rf of 0.4 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N16,N20-tetra(p-toluenesulfonyl)-1,20-di(ethylamino)- 5,16 -diazaeicosane (14h, 0.177 g, yield: 98%). The results of elementary analysis of Compound 14h are shown in Table 4 below, and the results of $^1$H-NMR and $^{13}$C-NMR of the same are shown in Table 9 below, respectively. The obtained Compound 14h (167 mg) was heated with phenol (0.318 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 15h (see Scheme 3) as colorless powder.

Example 4

Synthesis of 1,12-di (cyclopropylmethylamino)-4,9-diazadodecane HBr Salt (17) (Scheme 4)
Scheme 4

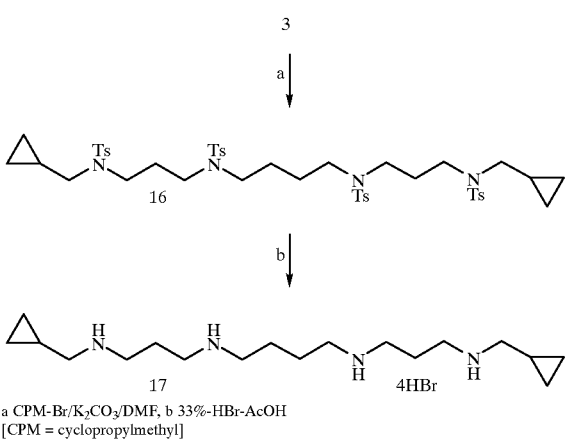

a CPM-Br/K₂CO₃/DMF, b 33%-HBr-AcOH
[CPM = cyclopropylmethyl]

A mixture of Compound 3 synthesized in Example 1 (0.100 g), anhydrous potassium carbonate (0.090 g) and bromomethylcyclopropane (35 ml) was allowed to react in DMF (40 ml) at room temperature for 3 days with stirring, filtered, and then concentrated. A substance exhibiting Rf of 0.8 in TLC (Merck, Art. 5715, chloroform:acetone (95:5 v/v)) was collected by silica gel column chromatography (Merck, Art. 7734, 70–230mesh) using chloroform:acetone (95:5 v/v) as a developing solvent to obtain N1,N4,N19,N12-tetra(p-toluenesulfonyl)-1,12-di(cyclopropylm ethylamino)-4,9-diazadodecane (16, 0.079 g, yield: 70%). The results of elementary analysis of Compound 16 are shown in Table 5 below, and the results of $^1$H-NMR and $^{13}$C-NMR of the same are shown in Table 10 below, respectively. The obtained Compound 16 (161 mg) was heated with phenol (0.206 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 17 (see Scheme 4) as colorless powder.

Example 5

Synthesis of 1,8-di(cyclopropylmethylamino)-4-azaoctane HBr Salt (19) (Scheme 5)
Scheme 5

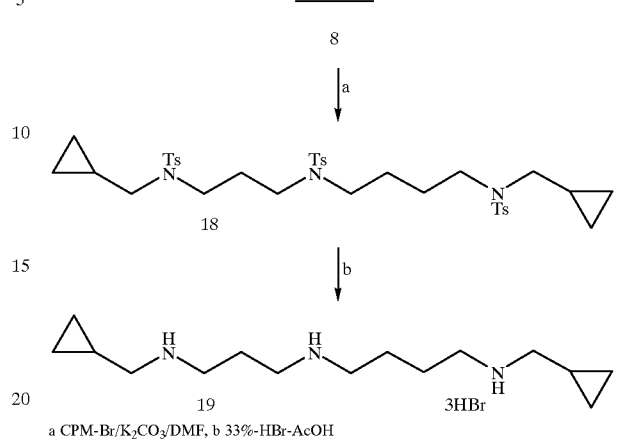

a CPM-Br/K₂CO₃/DMF, b 33%-HBr-AcOH

A mixture of Compound 8 synthesized in Example 2 (0.100 g), anhydrous potassium carbonate (0.107 g) and bromomethylcyclopropane (39 ml) was allowed to react in DMF (40 ml) at room temperature for 3 days with stirring, filtered, and then concentrated. A substance exhibiting Rf of 0.8 in TLC (Merck, Art. 5715, chloroform:acetone(95:5 v/v)) was collected by silica gel column chromatography (Merck, Art. 7734, 70–230mesh) using chloroform:acetone (95:5 v/v) as a developing solvent to obtain N1,N4,N8-tri(p-toluenesulfonyl)-1,8-di(cyclopropylmethylami no)-4-azaoctane (18, 0.062 g, yield: 53%). The results of elementary analysis of Compound 18 are shown in Table 5 below, and the results of $^1$H-NMR and $^{13}$C-NMR of the same are shown in Table 10 below, respectively. The obtained Compound 18 (97 mg) was heated with phenol (0.255 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 19 (see Scheme 5) as colorless powder.

Example 6.1

Synthesis of 1,13-di(cyclopropylmethylamino)-5,9-diazatridecane HBr Salt (21a) (Scheme 6)
Scheme 6

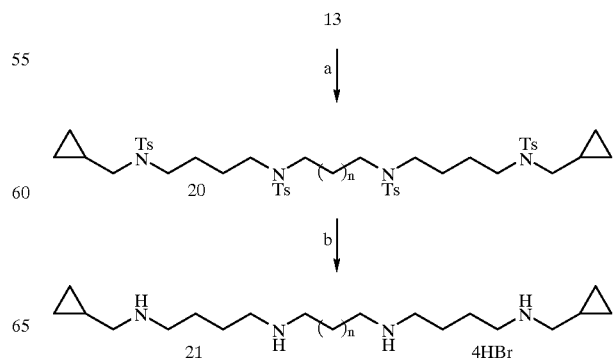

-continued a COM-Br/K$_2$CO$_3$/DMF, b 33%-HBr-AcOH $$\begin{bmatrix} a\ n = 1, b\ n = 2, c\ n = 3, \\ d\ n = 4, e\ n = 5, f\ n = 6, \\ g\ n = 7, h\ n = 8 \end{bmatrix}$$

A mixture of Compound 13a synthesized in Example 3.1 (0.249 g), anhydrous potassium carbonate (0.207 g) and bromomethylcyclopropane (74 ml) was allowed to react in DMF (40 ml) at room temperature for 3 days with stirring, filtered, and then concentrated. A substance exhibiting Rf of 0.8 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N9,N13-tetra(p-toluenesulfonyl)-1,13-di(cyclopropylme thylamino)-5,9-diazatridecane (20a, 0.253 g, yield: 90%). The results of elementary analysis of Compound 20a are shown in Table 5 below, and the results of $^1$H-NMR and $^{13}$C-NMR of the same are shown in Table 10 below, respectively. The obtained Compound 20a (240mg) was heated with phenol (0.428 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 21a (see Scheme 6) as colorless powder.

Example 6.2

Synthesis of 1,14-di(cyclopropylmethylamino)-5,10-diazatetradecane HBr Salt (21b) (Scheme 6)

A mixture of Compound 13b synthesized in Example 3.2 (0.100 g), anhydrous potassium carbonate (0.096 g) and bromomethylcyclopropane (34 ml) was allowed to react in DMF (40 ml) at room temperature for 3 days with stirring, filtered, and then concentrated. A substance exhibiting Rf of 0.8in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N10,N14-tetra(p-toluenesulfonyl)-1,14-di(cyclopropylm ethylamino)-5,10-diazatetradecane (20b, 0.109 g, yield: 93%). The results of elementary analysis of Compound 20b are shown in Table 5 below, and the results of $^1$H-NMR and $^{13}$C-NMR of the same are shown in Table 10 below, respectively. The obtained Compound 20b (175 mg) was heated with phenol (0.345 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 21b (see Scheme 6) as colorless powder.

Example 6.3

Synthesis of 1,15-di(cyclopropylmethylamino)-5,11-diazapentadecane HBr Salt (21c) (Scheme 6)

A mixture of Compound 13c synthesized in Example 3.3 (0.100 g), anhydrous potassium carbonate (0.085 g) and bromomethylcyclopropane (33 ml) was allowed to react in DMF (40 ml) at room temperature for 3 days with stirring, filtered, and then concentrated. A substance exhibiting Rf of 0.8in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N11,N15-tetra(p-toluenesulfonyl)-1,15-di(cyclopropylm ethylamino)-5,11-diazapentadecane (20c, 0.100 g, yield: 89%). The results of elementary analysis of Compound 20c are shown in Table 5 below, and the results of $^1$H-NMR and $^{13}$C-NMR of the same are shown in Table 10 below, respectively. The obtained Compound 20c (151 mg) was heated with phenol (0.293 g) in 33% HBr in acetic acid (10 ml) with stirring on an oil bath at 75° C. for 20 hours, and then the reaction mixture was concentrated under reduced pressure. The residue was added with diethylether and stirred, and the supernatant was discarded. This washing procedure was repeated by using a mixed solution of methanol and diethyl ether until the supernatant became colorless. The solvent was evaporated under reduced pressure to obtain Compound 21c (see Scheme 6) as colorless powder.

Example 6.4

Synthesis of 1,16-di(cyclopropylmethylamino)-5,12-diazahexadecane HBr Salt (21d) (Scheme 6)

A mixture of Compound 13d synthesized in Example 3.4 (0.194 g), anhydrous potassium carbonate (0.153 g) and bromomethylcyclopropane (55 ml) was allowed to react in DMF (40 ml) at room temperature for 3 days with stirring, filtered, and then concentrated. A substance exhibiting Rf of 0.8 in TLC (Merck, Art. 5715, chloroform:acetone (95:5 v/v)) was collected by silica gel column chromatography (Merck, Art. 7734, 70–230mesh) using chloroform:acetone (95:5 v/v) as a developing solvent to obtain N1,N5,N12,N16-tetra(p-toluenesulfonyl)-1,16-di(cyclopropylm ethylamino)-5,12-diazahexadecane (20d, 0.159 g, yield: 73%). The results of elementary analysis of Compound 20d are shown in Table 5 below, and the results of $^1$H-NMR and $^{13}$C-NMR of the same are shown in Table 11 below, respectively. The obtained Compound 20d (149 mg) was heated with phenol (0.285 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 21d (see Scheme 6) as colorless powder.

Example 6.5

Synthesis of 1,17-di(cyclopropylmethylamino)-5,13-diazaheptadecane HBr Salt (21e) (Scheme 6)

A mixture of Compound 13e synthesized in Example 3.5 (0.185 g), anhydrous potassium carbonate (0.143 g) and bromomethylcyclopropane (52 ml) was allowed to react in DMF (40 ml) at room temperature for 3 days with stirring, filtered, and then concentrated. A substance exhibiting Rf of 0.8in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N13,N17-tetra(p-toluenesulfonyl)-1,17-di(cyclopropylmethylamino)-5,13-diazaheptadecane (20e, 0.149 g, yield: 72%). The results of elementary analysis of Compound 20e are shown in Table 5 below, and the results of $^1$H-NMR and $^{13}$C-NMR of the same are shown in Table 11 below, respectively. The obtained Compound 20e (139 mg) was heated with phenol (0.262 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 21e (see Scheme 6) as colorless powder.

Example 6.6

Synthesis of 1,18-di(cyclopropylmethylamino)-5,14-diazaoctadecane HBr Salt (21f) (Scheme 6)

A mixture of Compound 13f synthesized in Example 3.6 (0.100 g), anhydrous potassium carbonate (0.120 g) and bromomethylcyclopropane (45 ml) was allowed to react in DMF (40 ml) at room temperature for 3 days with stirring, filtered, and then concentrated. A substance exhibiting Rf of 0.8in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N14,N18-tetra(p-toluenesulfonyl)-1,18-di(cyclopropylmethylamino)-5,14-diazaoctadecane (20f, 0.085 g, yield: 92%). The results of elementary analysis of Compound 20f are shown in Table 5 below, and the results of $^1$H-NMR and $^{13}$C-NMR of the same are shown in Table 11 below, respectively. The obtained Compound 20f (174 mg) was heated with phenol (0.324 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 21f (see Scheme 6) as colorless powder.

Example 6.7

Synthesis of 1,19-di(cyclopropylmethylamino)-5,15-diazanonadecane HBr Salt (21 g) (Scheme 6)

A mixture of Compound 13 g synthesized in Example 3.7 (0.186 g), anhydrous potassium carbonate (0.140 g) and bromomethylcyclopropane (51 ml) was allowed to react in DMF (40 ml) at room temperature for 3 days with stirring, filtered, and then concentrated. A substance exhibiting Rf of 0.8 in TLC (Merck, Art. 5715, chloroform:acetone (95:5 v/v)) was collected by silica gel column chromatography (Merck, Art. 7734, 70–230mesh) using chloroform:acetone (95:5 v/v) as a developing solvent to obtain N1,N5,N15,N19-tetra(p-toluenesulfonyl)-1,19-di(cyclopropylmethylamino)-5,15-diazanonadecane (20 g, 0.177 g, yield: 85%). The results of elementary analysis of Compound 20 g are shown in Table 5 below, and the results of $^1$H-NMR and $^{13}$C-NMR of the same are shown in Table 11 below, respectively. The obtained Compound 20 g (167 mg) was heated with phenol (0.306 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 21 g (see Scheme 6) as colorless powder.

Example 6.8

Synthesis of 1,20-di(cyclopropylmethylamino)-5,16-diazatetradecane HBr Salt (21h) (Scheme 6)

A mixture of Compound 13h synthesized in Example 3.8 (0.146 g), anhydrous potassium carbonate (0.108 g) and bromomethylcyclopropane (39 ml) was allowed to react in DMF (40 ml) at room temperature for 3 days with stirring, filtered, and then concentrated. A substance exhibiting Rf of 0.8 in TLC (Merck, Art. 5715, chloroform:acetone (95:5 v/v)) was collected by silica gel column chromatography (Merck, Art. 7734, 70–230 mesh) using chloroform:acetone (95:5 v/v) as a developing solvent to obtain N1,N5,N16,N20-tetra(p-toluenesulfonyl)-1,20-di(cyclopropylmethylamino)-5,16-diazaeicosane (20h, 0.133 g, yield: 82%). The results of elementary analysis of Compound 20h are shown in Table 5 below, and the results of $^1$H-NMR and $^{13}$C-NMR of the same are shown in Table 11 below, respectively. The obtained Compound 20h (123mg) was heated with phenol (0.222 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 21h (see Scheme 6) as colorless powder.

Example 7.1

Synthesis of 1-ethylamino-8-amino-4-azaoctane HBr Salt (25) (Scheme 7)

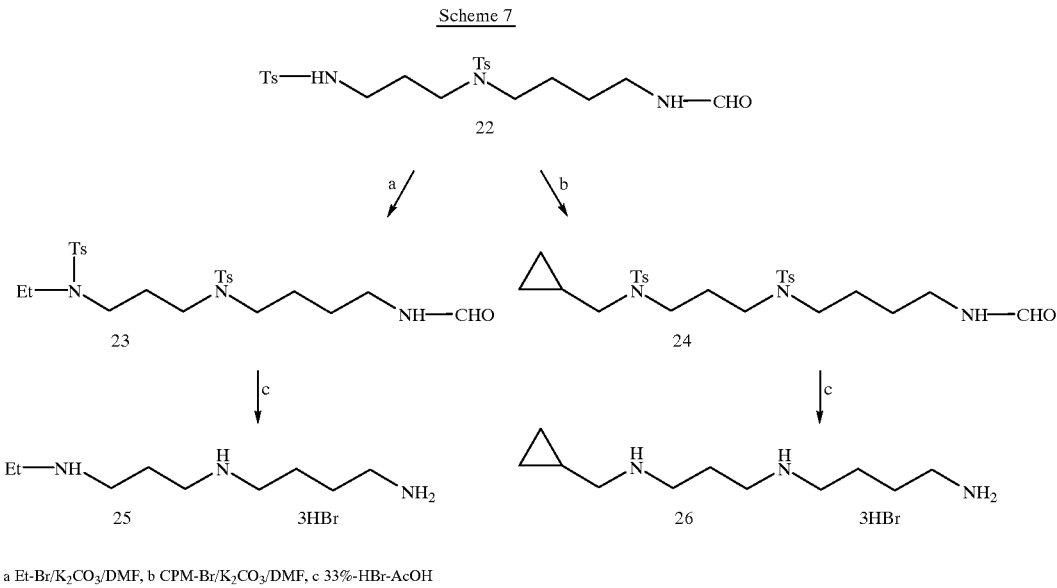

a Et-Br/K$_2$CO$_3$/DMF, b CPM-Br/K$_2$CO$_3$/DMF, c 33%-HBr-AcOH

First, using diaminopropane as a raw material, N1,N4-di(p-toluenesulfonyl)-N8-formyl-1,8-diamino-4-azaoctane (22) was derived according to the method described in Reference 8.

Subsequently, a mixture of the above Compound 22 (0.236 g), anhydrous potassium carbonate (0.339 g) and bromoethane (91 ml) was allowed to react in DMF (50 ml) at room temperature for 3 days with stirring, filtered, and then concentrated. A substance exhibiting Rf of 0.3 in TLC (Merck, Art. 5715, chloroform:acetone (9:1 v/v)) was collected by silica gel column chromatography (Merck, Art. 7734, 70–230 mesh) using chloroform:acetone (7:3 v/v) as a developing solvent to obtain N1-ethyl-N1,N4-di(p-toluenesulfonyl)-N8-formyl-1,8-diamino-4-azaoctane (23, 0.221 g, yield: 88%). The results of elementary analysis of Compound 23 are shown in Table 6 below, and the results of $^1$H-NMR and $^{13}$C-NMR of the same are shown in Table 12 below, respectively. The obtained Compound 23 (210mg) was heated with phenol (0.929 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 25 (see Scheme 7) as colorless powder.

Example 7.2

Synthesis of 1-cyclopropylmethylamino-8-amino-4-azaoctane HBr Salt (26) (Scheme 7)

A mixture of Compound 22 synthesized in Example 7.1 (0.187 g), anhydrous potassium carbonate (0.268 g) and bromomethylcyclopropane (97 ml) was allowed to react in DMF (50 ml) at room temperature for 3 days with stirring, filtered, and then concentrated. A substance exhibiting Rf of 0. 3 in TLC (Merck, Art. 5715, chloroform:acetone (9:1 v/v)) was collected by silica gel column chromatography (Merck, Art. 7734, 70–230 mesh) using chloroform:acetone (7:3 v/v) as a developing solvent to obtain N1-cyclopropylmethyl-N1,N4-di(p-toluenesulfonyl)-N8-formyl-1,8-diamino-4-azaoctane (24, 0.147 g, yield: 71%). The results of elementary analysis of Compound 24 are shown in Table 6 below, and the results of $^1$H-NMR and $^{13}$C-NMR of the same are shown in Table 12 below, respectively. The obtained Compound 24 (135 mg) was heated with phenol (0.563 g) with stirring in 33% HBr in acetic acid (10 ml) on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 26 (see Scheme 7) as colorless powder.

Example 8.1

Synthesis of 1,7-di(ethylamino)-4-benzyl-4-azaheptane HBr Salt (30) (Scheme 8)

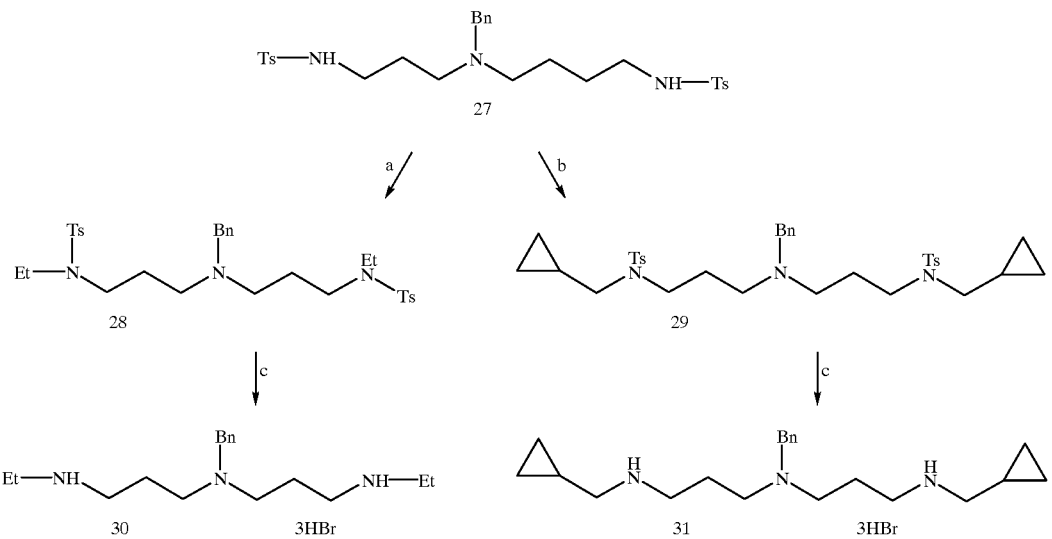

a Et-Br/K₂CO₃/DMF, b CPM-Br/K₂CO₃/DMF, c 33%-HBr-AcOH

First, using benzylamine and N-(p-toluenesulfonyl)-3-bromopropylamine as raw materials, N1,N7-di(p-toluenesulfonyl)-N4-benzyl-1,7-diamino-4-azaheptane (27) was prepared according to the method described in Patent Document 2.

Subsequently, a mixture of the above Compound 27 (0.200 g), anhydrous potassium carbonate (0.261 g) and bromoethane (70 ml) was allowed to react in DMF (50 ml) at room temperature for 3 days with stirring, filtered, and then concentrated. A substance exhibiting Rf of 0.7 in TLC (Merck, Art. 5715, chloroform:acetone (9:1 v/v)) was collected by silica gel column chromatography (Merck, Art. 7734, 70–230 mesh) using chloroform:acetone (9:1 v/v) as a developing solvent to obtain N1,N7-di(p-toluenesulfonyl)-N4-benzyl-1,7-di(ethylamino)-4-azaheptane (28, 0.160 g, yield: 72%). The results of elementary analysis of Compound 28 are shown in Table 6 below, and the results of ¹H-NMR and ¹³C-NMR of the same are shown in Table 12 below, respectively. The obtained Compound 28 (147 mg) was heated with phenol (0.472 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 30 (see Scheme 8) as colorless powder.

Example 8.2

Synthesis of 1,7-di(cyclopropylmethylamino)-4-benzyl-4-azaheptane HBr Salt (31) (Scheme 8)

A mixture of the above Compound 27 synthesized in Example 8.1 (0.339 g), anhydrous potassium carbonate (0.442 g) and bromomethylcyclopropane (160 ml) was allowed to react in DMF (50 ml) at room temperature for 3 days with stirring, filtered, and then concentrated. A substance exhibiting Rf of 0.8 in TLC (Merck, Art. 5715, chloroform:acetone (9:1 v/v)) was collected by silica gel column chromatography (Merck, Art. 7734, 70–230 mesh) using chloroform:acetone (9:1 v/v) as a developing solvent to obtain N1,N7-di(p-toluenesulfonyl)-N4-benzyl-1,7-di(cyclopropylmet hylamino)-4-azaheptane (29, 0.255 g, yield: 63%). The results of elementary analysis of Compound 29 are shown in Table 6 below, and the results of ¹H-NMR and ¹³C-NMR of the same are shown in Table 12 below, respectively. The obtained Compound 29 (240 mg) was heated with phenol (0.708 g) with stirring in 33% HBr in acetic acid (10 ml) on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 31 (see Scheme 8) as colorless powder.

Example 9.1

Synthesis of 1,15-di(ethylamino)-8-benzyl-4,8,12-triazapentadecane HBr Salt (35) (Scheme 9)

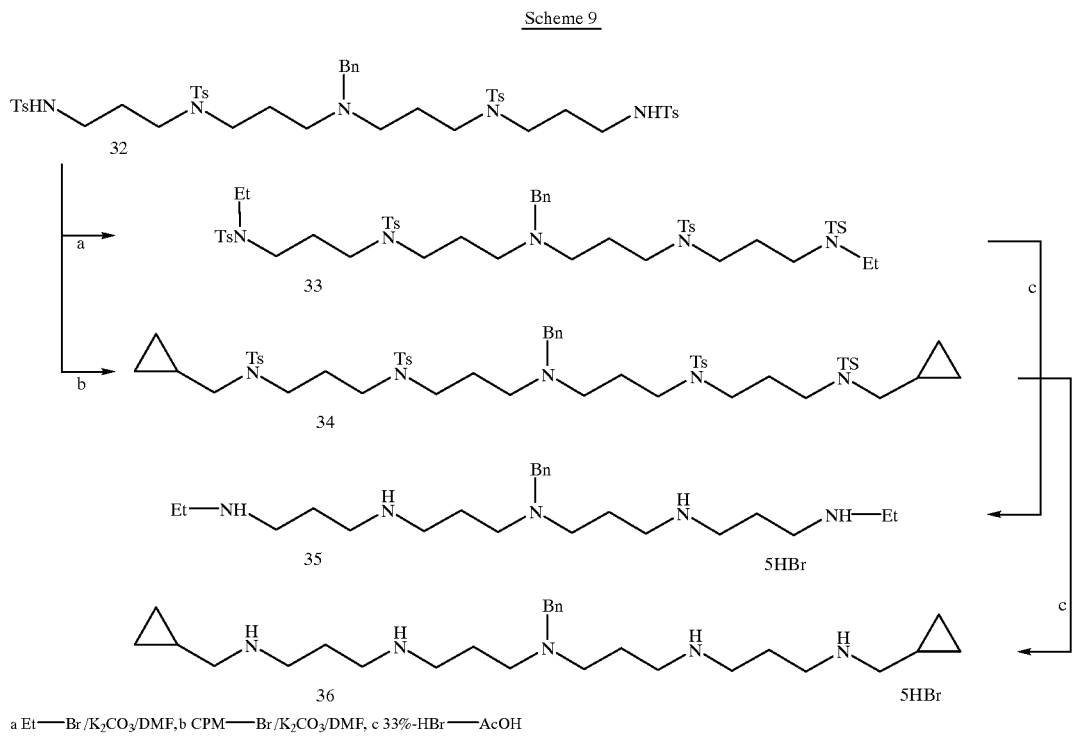

a Et—Br/K₂CO₃/DMF, b CPM—Br/K₂CO₃/DMF, c 33%-HBr—AcOH

First, using benzylamine as a raw material, N1,N4,N12,N15-tetra(p-toluenesulfonyl)-N8-benzyl-1,15-diamino-4, 8, 1 2-triazapentadecane (32) was prepared according to t he method described in Patent Document 2.

Subsequently, a mixture of the above Compound 32 (0.324 g), anhydrous potassium carbonate (0.218 g) and bromoethane (64 ml) was allowed to react in DMF (50 ml) at room temperature for 3 days with stirring, filtered, and then concentrated. A substance exhibiting Rf of 0.7 in TLC (Merck, Art. 5715, chloroform:acetone (9:1 v/v)) was collected by silica gel column chromatography (Merck, Art. 7734, 70–230 mesh) using chloroform:acetone (9:1 v/v) as a developing solvent to obtain N1,N4,N12,N15-tetra(p-toluenesulfonyl)-N8-benzyl-1,15-di(ethylamino)-4,8,12-triazapentadecane (33, 0.278 g, yield: 81%). The results of elementary analysis of Compound 33 are shown in Table 6 below, and the results of $^1$H-NMR and $^{13}$C-NMR of the same are shown in Table 12 below, respectively. The obtained Compound 33 (265 mg) was heated with phenol (0.495 g) with stirring in 33% HBr in acetic acid (10 ml) on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 35 (see Scheme 9) as colorless powder.

Example 9.2

Synthesis of 1,15-di(cyclopropylmethylamino)-8-benzyl-4,8,12-triazapentadecane HBr Salt (36) (Scheme 9)

A mixture of Compound 32 synthesized in Example 9.1 (0.168 g), anhydrous potassium carbonate (0.122 g) and bromomethylcyclopropane (44 ml) was allowed to react in DMF (50 ml) at room temperature for 3 days with stirring, filtered, and then concentrated. A substance exhibiting Rf of 0.8 in TLC (Merck, Art. 5715, chloroform:acetone (9:1 v/v)) was collected by silica gel column chromatography (Merck, Art. 7734, 70–230mesh) using chloroform:acetone (9:1 v/v) as a developing solvent to obtain N1,N4,N12,N15-tetra(p-toluenesulfonyl)-N8-benzyl-1,15-di(cyclopropylmethylamino)-4,8,12-triazapentadecane (34, 0.158 g, yield: 85%). The results of elementary analysis of Compound 34 are shown in Table 6 below, and the results of $^1$H-NMR and $^{13}$C-NMR of the same are shown in Table 13 below, respectively. The obtained Compound 34 (145 mg) was heated with phenol (0.257 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 36 (see Scheme 9) as dark brown hygroscopic powder.

Example 10.1

Synthesis of 1,17-di(ethylamino)-9-benzyl-5,9,13-triazaheptadecane HBr Salt (40) (Scheme 10)

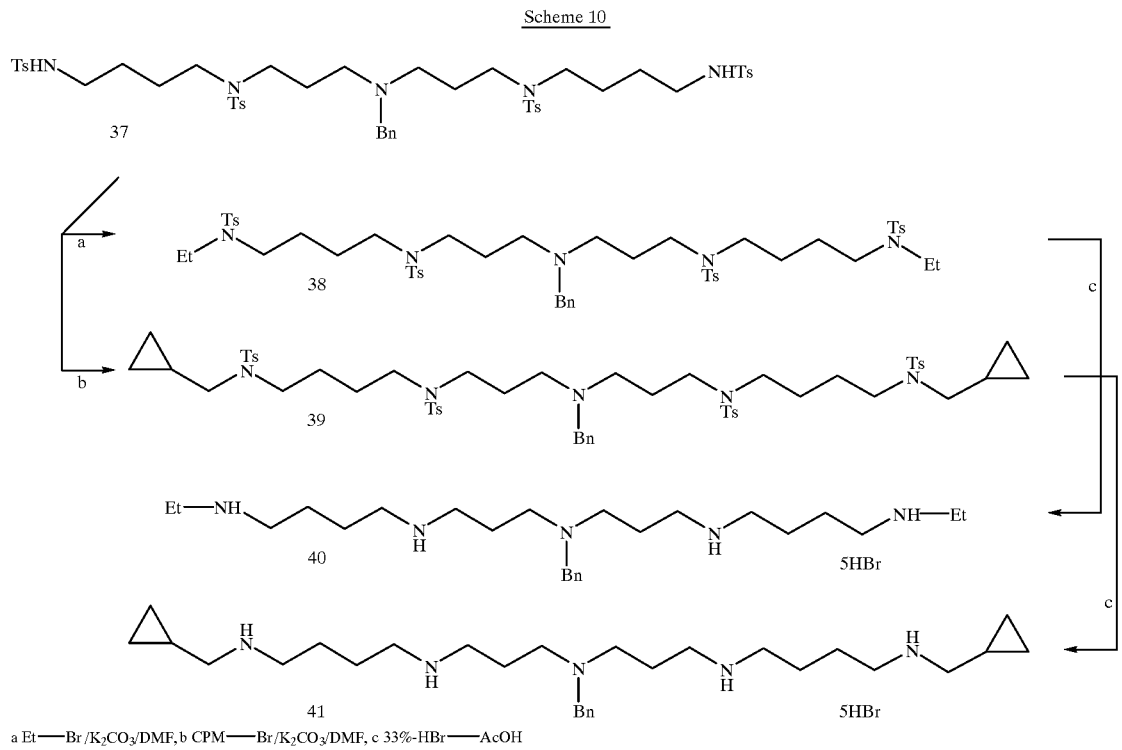

First, using benzylamine as a raw material, N1,N5,N13,N17-tetra(p-toluenesulfonyl)-N9-benzyl-1,17-diamino-5,9,13-triazaheptadecane (37) was prepared according to the method described in Patent Document 2.

Subsequently, a mixture of the above Compound 37 (0.259 g), anhydrous potassium carbonate (0.182 g) and bromoethane (49 ml) was allowed to react in DMF (50 ml) at room temperature for 3 days with stirring, filtered, and then concentrated. A substance exhibiting Rf of 0.7 in TLC (Merck, Art. 5715, chloroform:acetone (9:1 v/v)) was collected by silica gel column chromatography (Merck, Art. 7734, 70–230 mesh) using chloroform:acetone (9:1 v/v) as a developing solvent to obtain N1,N5,N13,N17-tetra(p-toluenesulfonyl)-N9-benzyl-1,17-di(ethylamino)-5,9,13-triazaheptadecane (38, 0.208 g, yield: 76%). The results of elementary analysis of Compound 38 are shown in Table 6 below, and the results of $^1$H-NMR and $^{13}$C-NMR of the same are shown in Table13below, respectively. The obtained Compound 38 (195 mg) was heated with phenol (0.354 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 40 (see Scheme 10) as colorless powder.

Example 10.2

Synthesis of 1,17-di(cyclopropylmethylamino)-9-benzyl-5,9,13-triazaheptadecane HBr Salt (41) (Scheme 10)

A mixture of Compound 37 synthesized in Example 10.1 (0.241 g), anhydrous potassium carbonate (0.170 g) and bromomethylcyclopropane (62 ml) was allowed to react in DMF (50 ml) at room temperature for 3 days with stirring, filtered, and then concentrated. A substance exhibiting Rf of 0.8 in TLC (Merck, Art. 5715, chloroform:acetone (9:1 v/v)) was collected by silica gel column chromatography (Merck, Art. 7734, 70–230 mesh) using chloroform:acetone (9:1 v/v) as a developing solvent to obtain N1,N5,N13,N17-tetra(p-toluenesulfonyl)-N9-benzyl-1,17-di(cyclopropylmethylamino)-5,9,13-triazaheptadecane (39, 0.203 g, yield: 76%). The results of elementary analysis of Compound 39 are shown in Table 6 below, and the results of $^1$H-NMR and $^{13}$C-NMR of the same are shown in Table 13 below, respectively. The obtained Compound 39 (190 mg) was heated with phenol (0.329 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 41 (see Scheme 10) as brown powder.

Example 11.1

Synthesis of 1,13-diamino-5,9-diazatridecane HBr Salt (42) (Scheme 11)

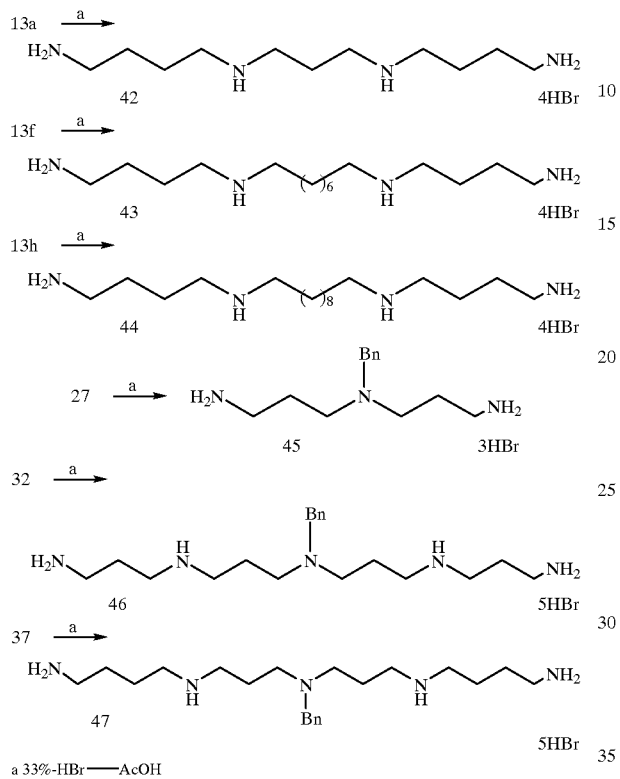

Scheme 11 a 33%-HBr—AcOH

Compound 13a a synthesize in Example 3.1 (252 mg) was heated with phenol (0.570 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 42 (see Scheme 11) as colorless powder.

Example 11.2

Synthesis of 1.18-diamino-5,4-diazaoctadecane HBr Salt (43) (Schem 11)

Compound 13f sysnthesized in Example 3.6 (152mg) was heated with phenol (0.317 g) in 33% HBr in acetic acid (10 ml) with stirring on an oil bath at 75° C. for 20 hours, and then the reaction reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 43 (see Scheme 11) as colorless powder.

Example 11.3

Synthesis of 1,20-diamino-5,16-diazaeicosane HBr Salt (44) (Scheme 11)

Compound 13h synthesized in Example 3.8 (185mg) was heated with phenol (0.374 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 44 (see Scheme 11) as colorless powder.

Example 11.4

Synthesis of N4-benzyl-1,7-diamino-4-azaheptane HBr Salt (45) (Scheme 11)

Compound 27 synthesized in Example 8 (239 mg) was heated with phenol (0.849 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 45 (see Scheme 11) as brown hygroscopic powder.

Example 11.5

Synthesis of N8-benzyl-1,15-diamino-4,8,12-triazapentadecane HBr Salt (46) (Scheme 11)

Compound 32 synthesized in Example 9 (225 mg) was heated with phenol (0.445 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 46 (see Scheme 11) as dark brown hygroscopic powder.

Example 11.6

Synthesis of N9-benzyl-1,17-diamino-5,9,13-triazaheptadecane HBr Salt (47) (Scheme 11)

Compound 37 synthesized in Example 10 (215 mg) was heated with phenol (0.413 g) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 47 (see Scheme 11) as dark brown hygroscopic powder.

Example 12.1

Synthesis of N1,N8-di(p-toluenesulfonyl)-di(ethylamino)-octane (48a) and N1,N8-di(ethylamino)-octane (48b) HBr Salt (Scheme 12)

Scheme 12

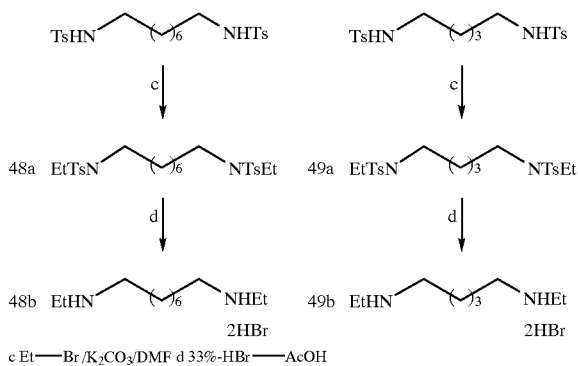

c Et—Br/K$_2$CO$_3$/DMF  d 33%-HBr—AcOH

First, using 1,8-diaminooctane as a raw material, N1,N8-di(p-toluenesulfonyl)-1,8-diaminooctane was prepared according to the method described in M. Iwata and H. Kuzuhara, Bull. Chem. Soc. Jpn., 55, pp.2153–2157 (1982).

Subsequently, a mixture of the above N1,N8-di(p-toluenesulfonyl)-1,8-diaminooctane (1.0 g), anyhydrous postassium carbonate (1.54 g) and bromoethane (2.5molar equivalents) was allowed to react in DMF (60 ml) at room temperature for 3 days with stirring, filtered, and then concentrated. A substance exhibiting Rf of 0.7 in TLC (Merck, Art. 5715, chloroform:acetone (98:2 v/v)) was collected by silica gel column chromatography (Merck, Art. 7734, 70–230mesh) using chloroform:acetone (98:2 v/v) as a developing solvent to obtain N1,N8-di(p-toluenesulfonyl)-1,8-di(ethylamino)octane (48a, 0.901 g, mp:112–3° C. (recrystallized from a mixture of acetone and methanol)). The obtained Compound 48a (876 mg) was heated with phenol (20 molar equivalents) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 48b (see Scheme 12) as colorless powder.

Example 12.2

Synthesis of N1,N5-di(p-toluenesulfonyl)-di(ethylamino)pentane (49a) and N1,N5-di(ethylamino)pentane HBr Salt (49b) (Scheme 12)

First, using 1,5-diaminopentane as a raw material, N1,N5-di(p-toluenesulfonyl)-1,5-diaminopentane was prepared according to the method described in M. Iwata and H. Kuzuhara, Bull. Chem. Soc. Jpn., 55, pp.2153–2157 (1982).

Subsequently, a mixture of the above N1,N5-di(p-toluenesulfonyl)-1,5-diaminopentane (1.0 g), anhydrous potassium carbonate (1.683 g) and bromoethane (0.454 ml) was allowed to react in DMF (40 ml) at room temperature for 3 days with stirring, filtered, and then concentrated. A substance exhibiting Rf of 0.7 in TLC (Merck, Art. 5715, chloroform:acetone (98:2 v/v)) was collected by silica gel column chromatography (Merck, Art. 7734, 70–230 mesh) using chloroform:acetone (98:2 v/v) as a developing solvent to obtain N1,N5-di(p-toluenesulfonyl)-1,5-di(ethylamino)pentane (49a, 0.901 g, mp:112–3° C. (recrystallized from a mixture of acetone and methanol)). The obtained Compound 49a (744 mg) was heated with phenol (20 molar equivalents) in 33% HBr in acetic acid (10 ml) with stirring on an oil bath at 75° C. for 20 hours, and then the reaction mixture was concentrated under reduced pressure. The residue was added with diethyl ether and stirred, and the supernatant was discarded. This washing procedure was repeated by using a mixed solution of methanol and diethyl ether until the supernatant became colorless. The solvent was evaporated under reduced pressure to obtain Compound 49b (see Scheme 12) as colorless powder.

Physicochemical Analysis

To characterize the novel compounds, physicochemical analyses using elementary analysis and $^1$H-NMR and $^{13}$C-NMR spectrum analyses were performed for precursors subjected to detosylation reaction. The results are shown in Tables 4 to 6 and 8 to 13. The yields of the precursors are also shown in Tables 4 to 6. The yields of detosylation reaction in which detosylated compounds were obtained from the precursors are shown in Table 7. The yields and the results of elementary analyses of the precursors 4, 9, 14a, 14b, 14c, 14d, 14e, 14f, 14 g, 14h, 48a and 49a, 16, 18, 20a, 20b, 20c, 20e, 20f, 20 g and 20h, as well as 23, 24, 28, 29, 33, 34, 38 and 39, which were subjected to detosylation reaction, are summarized in Tables 4 to 6.

The yields of detosylation reactions for deriving target compounds from the precursors are summarized in Table 7. The results of $^1$H-NMR and $^{13}$C-NMR spectrum analyses of the precursors 4, 9, 14a, 14b, 14c and 14d, 14e, 14f, 14 g, 14h, 48b and 49b, 16, 18, 20a, 20b and 20c, 20e, 20f, 20 g and 20h, 23, 24, 28, 29 and 33, as well as 34, 38 and 39, which were subjected to detosylation reaction, are summarized in Tables 8 to 13.

TABLE 4

| (yield/%) | 4 (58) C$_{42}$H$_{58}$N$_4$S$_4$O$_8$ | | 9 (65) C$_{32}$H$_{45}$N$_3$S$_3$O$_8$ | | 14a (88) C$_{43}$H$_{60}$N$_4$S$_4$O$_8$ | | 14b (65) C$_{44}$H$_{62}$N$_4$S$_4$O$_8$ | |
|---|---|---|---|---|---|---|---|---|
| | Found | Calcd | Found | Calcd | Found | Calcd | Found | Calcd |
| C/% | 57.46 | 57.64 | 58.61 | 57.89 | 57.94 | 58.08 | 58.43 | 58.51 |
| H/% | 6.60 | 6.68 | 6.88 | 6.83 | 6.82 | 6.80 | 6.89 | 6.92 |
| N/% | 6.39 | 6.40 | 6.32 | 6.33 | 6.34 | 6.30 | 6.18 | 6.20 |
| | 14c (87) C$_{45}$H$_{64}$N$_4$S$_4$O$_8$ | | 14d (99) C$_{46}$H$_{66}$N$_4$S$_4$O$_8$ | | 14e (89) C$_{47}$H$_{68}$N$_4$S$_4$O$_8$ | | 14f (92) C$_{48}$H$_{70}$N$_4$S$_4$O$_8$ | |
| C/% | 58.75 | 58.92 | 59.24 | 59.33 | 59.66 | 59.72 | 59.98 | 60.09 |
| H/% | 6.97 | 7.03 | 7.07 | 7.14 | 7.27 | 7.25 | 7.30 | 7.35 |
| N/% | 6.08 | 6.11 | 5.98 | 6.02 | 6.01 | 5.93 | 5.85 | 5.84 |

TABLE 4-continued

| | 14g (98)<br>$C_{49}H_{72}N_4S_4O_8$ | | 14h (98)<br>$C_{50}H_{74}N_4S_4O_8$ | | 48a (80)<br>$C_{26}H_{40}N_2S_2O_4$ | | 49a (72)<br>$C_{23}H_{34}N_2S_2O_4$ | |
|---|---|---|---|---|---|---|---|---|
| C/% | 60.28 | 60.46 | 60.94 | 60.82 | 61.35 | 61.38 | 59.12 | 59.20 |
| H/% | 7.42 | 7.46 | 7.59 | 7.55 | 7.95 | 7.93 | 7.38 | 7.34 |
| N/% | 5.74 | 5.76 | 5.60 | 5.67 | 5.45 | 5.51 | 5.93 | 6.00 |

TABLE 5

| (yield/%) | 16 (70)<br>$C_{46}H_{62}N_4S_4O_8$ | | 18 (53)<br>$C_{36}H_{49}N_3S_3O_6$ | | 20a (90)<br>$C_{43}H_{60}N_4S_4O_8$ | | 20b (93)<br>$C_{48}H_{66}N_4S_4O_6$ | |
|---|---|---|---|---|---|---|---|---|
| | Found | Calcd | Found | Calcd | Found | Calcd | Found | Calcd |
| C/% | 59.40 | 59.58 | 60.32 | 60.39 | 57.94 | 58.08 | 60.22 | 60.35 |
| H/% | 6.77 | 6.74 | 7.00 | 6.90 | 6.82 | 6.80 | 7.02 | 6.96 |
| N/% | 6.05 | 6.04 | 5.83 | 5.87 | 6.34 | 6.30 | 5.86 | 5.87 |

| | 20c (89)<br>$C_{49}H_{68}N_4S_4O_8$ | | 20d (73)<br>$C_{50}H_{70}N_4S_4O_8$ | | 20e (72)<br>$C_{51}H_{72}N_4S_4O_8$ | | 20f (76)<br>$C_{52}H_{74}N_4S_4O_8$ | |
|---|---|---|---|---|---|---|---|---|
| C/% | 60.45 | 60.71 | 60.94 | 61.07 | 61.32 | 61.42 | 61.57 | 61.75 |
| H/% | 7.12 | 7.07 | 7.17 | 7.18 | 7.25 | 7.28 | 7.38 | 7.37 |
| N/% | 5.72 | 5.78 | 5.67 | 5.70 | 5.59 | 5.62 | 5.35 | 5.54 |

| | 20g (85)<br>$C_{53}H_{76}N_4S_4O_8$ | | 20h (82)<br>$C_{54}H_{78}N_4S_4O_8$ | |
|---|---|---|---|---|
| C/% | 62.15 | 62.08 | 62.30 | 62.40 |
| H/% | 7.48 | 7.47 | 7.57 | 7.56 |
| N/% | 5.43 | 5.46 | 5.41 | 5.39 |

| (yield/%) | 23 (88)<br>$C_{24}H_{35}N_3S_2O_5$ | | 24 (71)<br>$C_{26}H_{37}N_3S_2O_5$ | | 28 (72)<br>$C_{31}H_{43}N_3S_2O_4$ | | 29 (63)<br>$C_{35}H_{47}N_3S_2O_4$ | |
|---|---|---|---|---|---|---|---|---|
| | Found | Calcd | Found | Calcd | Found | Calcd | Found | Calcd |
| C/% | 56.57 | 56.56 | 58.41 | 58.29 | 63.49 | 63.56 | 65.94 | 65.90 |
| H/% | 6.97 | 6.92 | 7.07 | 6.96 | 7.39 | 7.40 | 7.47 | 7.43 |
| N/% | 7.99 | 8.24 | 7.81 | 7.84 | 7.25 | 7.17 | 6.51 | 6.59 |

| | 33 (81)<br>$C_{51}H_{69}N_5S_4O_8$ | | 34 (85)<br>$C_{56}H_{73}N_5S_4O_8$ | | 38 (76)<br>$C_{53}H_{47}N_5S_4O_8$ | | 39 (76)<br>$C_{57}H_{77}N_5S_4O_8$ | |
|---|---|---|---|---|---|---|---|---|
| C/% | 60.59 | 60.75 | 62.16 | 62.29 | 61.32 | 61.42 | 62.85 | 62.90 |
| H/% | 6.80 | 6.90 | 6.85 | 6.94 | 7.01 | 7.10 | 7.08 | 7.13 |
| N/% | 6.85 | 6.95 | 6.53 | 6.60 | 6.77 | 6.76 | 6.34 | 6.43 |

TABLE 7

| Compnd | Yield/% | Compnd | Yield/% | Compnd | Yield/% | Compnd | Yield/% |
|---|---|---|---|---|---|---|---|
| 5 | 87 | 15h | 90 | 21g | 85 | 41 | 87 |
| 10 | 91 | 17 | 90 | 21h | 82 | 42 | 88 |
| 15a | 94 | 19 | 93 | 25 | 91 | 43 | 94 |
| 15b | 91 | 21a | 96 | 26 | 78 | 44 | 87 |
| 15c | 88 | 21b | 93 | 30 | 97 | 45 | 97 |
| 15d | 89 | 21c | 89 | 31 | 99 | 46 | 87 |
| 15e | 91 | 21d | 73 | 35 | 92 | 47 | 87 |

TABLE 7-continued

| Compnd | Yield/% | Compnd | Yield/% | Compnd | Yield/% | Compnd | Yield/% |
|---|---|---|---|---|---|---|---|
| 15f | 85 | 21e | 72 | 36 | 88 | 48b | 96 |
| 15g | 89 | 21f | 76 | 49 | 86 | 49b | 95 |

| | $^1$H—NMR | | | | | $^{13}$C—NMR | | | | |
|---|---|---|---|---|---|---|---|---|---|---|
| Compnd | Et | —(CH$_2$)$_3$— | —(CH$_2$)$_2$— | aromatic | aromatic | Et | —(CH$_2$)$_3$— | —(CH$_2$)$_2$— | aromatic | aromatic |
| 4 | 1.07, t | 1.86, quin | 1.58, m | 2.41, s | 7.31, d | 13.91 | 28.71 | 25.75 | 21.48 | 136.20 |
| | 3.19, quar | 3.11, t | 3.10, quin | 2.42, s | 7.66, d | 43.14 | 45.46 | 48.39 | 127.07 | 136.65 |
| | J = 7.32 | 3.13, t | J = 7.32 | 7.29, d | 7.67, d | | 46.51 | | 127.12 | 143.16 |
| | | J = 7.32 | | J = 8.30 | J = 8.30 | | | | 129.69 | 143.31 |
| | | | | | | | | | 129.77 | |

| | $^1$H—NMR | | | | | $^{13}$C—NMR | | | | |
|---|---|---|---|---|---|---|---|---|---|---|
| Compnd | Et | —(CH$_2$)$_4$— | —(CH$_2$)$_3$— | aromatic | aromatic | Et | —(CH$_2$)$_4$— | —(CH$_2$)$_3$— | aromatic | aromatic |
| 9 | 1.08, t | 1.57, m | 1.87, quin | 2.42, s | 7.31, d | 13.91 | 25.65 | 28.69 | 21.47 | 129.75 |
| | 1.09, t | 3.12, t | 3.13, t | 2.43, s | 7.67, d | 14.00 | 25.75 | 46.91 | 127.04 | 136.27 |
| | 3.18, quar | 3.12, t | 3.15, t | 7.29, d | 7.67, d | 42.84 | 45.44 | 48.40 | 127.07 | 136.66 |
| | 3.21, quar | J = 7.32 | J = 7.32 | J = 8.30 | 7.68, d | 43.12 | 46.43 | | 127.12 | 136.98 |
| | J = 7.32 | | | | J = 8.30 | | | | 129.65 | 143.05 |
| | | | | | | | | | 129.69 | 143.18 |
| | | | | | | | | | | 143.31 |

| | $^1$H—NMR | | | | | $^{13}$C—NMR | | | | |
|---|---|---|---|---|---|---|---|---|---|---|
| Compnd | Et | —(CH$_2$)$_4$— | —(CH$_2$)$_n$— | aromatic | aromatic | Et | —(CH$_2$)$_4$— | —(CH$_2$)$_n$— | aromatic | aromatic |
| 14a | 1.05, t | 1.57, quin | 1.86, quin | 2.41, s | 7.30, d | 13.98 | 25.56 | 28.67 | 21.47 | 136.32 |
| | 3.17, quar | 3.11~3.13, m | 3.14, t | 2.42, s | 7.67, d | 42.81 | 25.75 | 48.27 | 127.12 | 136.99 |
| | J = 7.32 | J = 7.32 | J = 7.32 | 7.28, d | 7.67, d | | 46.40 | | 129.65 | 143.03 |
| | | | | J = 8.30 | J = 8.30 | | 46.91 | | 129.75 | 143.29 |
| 14b | 1.05, t | 1.55~1.57, m | 1,56, m | 2.41, s | 7.30, d | 13.96 | 25.73 | 25.94 | 21.48 | 136.63 |
| | 3.17, quar | 3.11~3.13, m | 3.10~3.13, m | 2.42, s | 7.67, d | 42.78 | 25.79 | 48.02 | 127.04 | 137.01 |
| | J = 7.32 | J = 7.32 | | 7.28, d | 7.68, d | | 46.94 | | 127.09 | 143.03 |
| | | | | J = 8.30 | J = 8.30 | | | | 129.64 | 143.18 |
| | | | | | | | | | 129.70 | |
| 14c | 1.05, t | 1.55~1.57, m | 1.26, quin | 2.41, s | 7.30, d | 13.98 | 25.73 | 23.80 | 21.47 | 136.68 |
| | 3.17, quar | 3.11~3.13, m | 1.53, quin | 2.42, s | 7.67, d | 42.79 | 25.79 | 28.41 | 127.02 | 136.99 |
| | J = 7.32 | J = 7.32 | 3.06, t | 7.28, d | 7.68, d | | 46.97 | 48.42 | 127.07 | 143.03 |
| | | | J = 7.32 | J = 8.30 | J = 8.30 | | 47.96 | | 129.64 | 143.13 |
| | | | | | | | | | 129.67 | |
| 14d | 1.06, t | 1.57~1.58, m | 1.26, quin | 2.41, s | 7.30, d | 14.00 | 25.75 | 26.30 | 21.47 | 136.76 |
| | 3.17, quar | 3.11, t | 1.50, quin | 2.42, s | 7.67, d | 42.79 | 25.79 | 28.71 | 127.04 | 137.01 |
| | J = 7.32 | 3.12, t | 3.06, t | 7.28, d | 7.67, d | | 46.99 | 48.42 | 127.07 | 143.03 |

| | $^1$H—NMR | | | | | $^{13}$C—NMR | | | | |
|---|---|---|---|---|---|---|---|---|---|---|
| Compnd | Et | —(CH$_2$)$_4$— | —(CH$_2$)$_n$— | aromatic | aromatic | Et | —(CH$_2$)$_4$— | —(CH$_2$)$_n$— | aromatic | aromatic |
| 14e | 1.07, t | J = 7.32 | J = 7.32 | J = 8.30 | | | 47.83 | | 129.65 | 143.10 |
| | 3.17, quar | 1.57~1.58, m | 1.23, quin | 2.42, s | 7.30, d | 14.00 | 25.78 | 26.63 | 21.47 | 136.80 |
| | J = 7.32 | 3.11, t | 1.25, quin | 7.29, d | 7.67, d | 42.78 | 46.99 | 28.69 | 127.04 | 137.01 |
| | | 3.13, t | 1.50, quin | J = 8.30 | J = 8.30 | | 47.80 | 28.76 | 127.07 | 143.06 |
| | | J = 7.32 | 3.06, t | | | | | 48.50 | 129.64 | |
| | | | J = 7.32 | | | | | | | |
| 14f | 1.07, t | 1.58, m | 1.24, m | 2.42, s | 7.29, d | 14.01 | 25.75 | 26.63 | 21.47 | 136.83 |
| | 3.18, quar | 3.12, t | 1.50, quin | 7.29, d | 7.67, d | 42.78 | 25.78 | 28.72 | 127.04 | 137.01 |
| | J = 7.32 | 3.13, t | 3.06, t | 7.67, d | J = 8.30 | | 46.99 | 29.10 | 127.07 | 143.05 |
| | | J = 7.32 | J = 7.32 | J = 8.30 | | | 47.74 | 48.50 | 129.64 | |
| 14g | 1.07, t | 1.57, m | 1.23, m | 2.42, s | | 14.01 | 25.75 | 26.72 | 21.47 | 136.84 |
| | 3.18, quar | 3.12, t | 1.49, quin | 7.29, d | | 42.78 | 25.78 | 28.74 | 127.04 | 137.01 |
| | J = 7.32 | 3.13, t | 3.06, t | 7.67, d | | | 46.99 | 29.10 | 127.07 | 143.03 |
| | | J = 7.32 | J = 7.32 | J = 8.30 | | | 47.71 | 29.43 | 129.62 | |
| | | | | | | | | 48.50 | | |

-continued

| | ¹H—NMR | | | | | ¹³C—NMR | | | | |
|---|---|---|---|---|---|---|---|---|---|---|
| Compnd | Et | —(CH₂)₄— | —(CH₂)ₙ— | aromatic | aromatic | Et | —(CH₂)₄— | —(CH₂)ₙ— | aromatic | aromatic |
| 14h | 1.07, t<br>3.18, quar<br>J = 7.32 | 1.57, m<br>3.12, t<br>3.13, t<br>J = 7.32 | 1.23, m<br>1.49, quin<br>3.06, t<br>J = 7.32 | 2.42, s<br>7.29, d<br>7.68, d<br>J = 8.30 | | 14.01<br>42.78 | 25.76<br>46.99 | 26.75<br>28.72<br>29.17<br>29.43<br>47.70<br>48.50 | 21.47<br>127.04<br>127.07<br>129.64 | 136.86<br>137.03<br>143.03 |
| 48b | 1.10, t<br>3.20, quar<br>J = 7.32 | | 1.26, m<br>1.52, quin<br>3.10, t<br>J = 7.32 | 2.42, s<br>7.29, d<br>7.68, d<br>J = 8.30 | | 14.06<br>42.59 | | 26.55<br>28.67<br>29.09<br>47.51 | 21.45<br>127.04<br>129.55<br>137.24 | 142.88 |
| 49b | 1.09, t<br>3.20, quar<br>J = 7.32 | | 1.32, quin<br>1.57, quin<br>3.10, t<br>J = 7.32 | 2.42, s<br>7.29, d<br>7.68, d<br>J = 8.30 | | 14.01<br>42.76 | | 23.67<br>28.39<br>47.37 | 21.47<br>127.04<br>129.60<br>137.09 | 142.98 |

| | ¹H—NMR | | | | | ¹³C—NMR | | | | |
|---|---|---|---|---|---|---|---|---|---|---|
| Compnd | C₄H₈— | —(CH₂)₃— | —(CH₂)₂— | aromatic | aromatic | C₄H₈— | —(CH₂)₃— | —(CH₂)₂— | aromatic | aromatic |
| 16 | 0.16, m<br>0.52, m<br>0.83, quin<br>3.00, d<br>J = 6.83 | 1.92, quin<br>3.15, t<br>3.22, t<br>J = 7.32 | 1.60, m<br>3.11, quin | 2.41, s<br>2.42, s<br>7.28, d<br>J = 7.32 | 7.30, d<br>7.66, d<br>7.67, d<br>J = 8.30 | 4.17<br>9.82<br>53.29 | 28.74<br>45.85<br>46.51 | 25.70<br>48.27 | 21.48<br>127.07<br>127.12<br>129.67<br>129.75 | 136.28<br>136.70<br>143.11<br>143.28 |

| Compnd | C₄H₈— | —(CH₂)₄— | —(CH₂)₃— | aromatic | aromatic | C₄H₈— | —(CH₂)₄— | —(CH₂)₃— | aromatic | aromatic |
|---|---|---|---|---|---|---|---|---|---|---|
| 18 | 0.16, m<br>0.50, m<br>0.83, quin<br>2.99, d<br>3.01, d<br>J = 6.83 | 1.59, m<br>3.14, t<br>3.15, t<br>J = 7.32 | 1.87, quin<br>3.21, t<br>3.22, t<br>J = 7.32 | 2.41, s<br>2.43, s<br>7.29, d<br>J = 7.32 | 7.31, d<br>7.67, d<br>7.68, d<br>J = 8.30 | 4.16<br>9.82<br>9.87<br>52.94<br>53.26 | 25.61<br>25.83<br>45.84<br>46.35<br>129.60 | 28.71<br>47.30<br>48.29<br>142.98 | 21.47<br>127.07<br>127.10<br>128.04<br>129.65 | 129.72<br>136.38<br>136.70<br>137.03<br>143.11<br>143.26 |

| Compnd | C₄H₈— | —(CH₂)₄— | —(CH₂)ₙ— | aromatic | aromatic | C₄H₈— | —(CH₂)₄— | —(CH₂)ₙ— | aromatic | aromatic |
|---|---|---|---|---|---|---|---|---|---|---|
| 20a | 0.14, m<br>0.47, m<br>0.82, quin<br>2.98, d<br>J = 6.83 | 1.59, quin<br>3.11~<br>3.13, m<br>J = 7.32 | 1.86, quin<br>3.21, t<br>J = 7.32 | 2.41, s<br>2.42, s<br>7.28, d<br>J = 8.30 | 7.30, d<br>7.67, d<br> | 4.16<br>9.85<br>52.91 | 25.56<br>25.75<br>46.31<br>47.30 | 28.66<br>48.29<br>127.12 | 21.47<br>21.50<br>127.05<br>143.28<br>129.62<br>129.75 | 136.35<br>137.04<br>142.98 |
| 20b | 0.14, m<br>0.47, m<br>0.82, quin<br>2.98, d<br>J = 6.83 | 1.55~<br>1.57, m<br>3.11<br>3.13, m<br>J = 7.32 | 1.56, m<br>3.21, m<br>J = 7.32<br>129.70 | 2.41, s<br>2.42, s<br>7.28, d<br>J = 8.30 | 7.30, d<br>7.67, d<br>7.68, d | 4.16<br>9.85<br>52.89 | 25.76<br>25.84<br>47.33<br>47.94 | 25.94<br>41.97<br>48.04 | 21.48<br>127.05<br>127.09<br>129.62 | 136.68<br>137.07<br>142.98<br>143.15 |
| 20c | 0.14, m<br>0.47, m<br>0.82, quin<br>2.98, d | 1.55~<br>1.57, m<br>3.12, t<br>3.21, t | 1.26, quin<br>1.55, quin<br>3.06, t<br>J = 7.32 | 2.41, s<br>2.42, s<br>7.28, d<br>J = 8.30 | 7.30, d<br>7.67, d<br>7.68, d | 4.16<br>9.85<br>52.89 | 25.76<br>25.84<br>47.35<br>47.97 | 23.82<br>28.41<br>48.34 | 21.48<br>127.05<br>129.60<br>129.67 | 136.73<br>137.07<br>142.98<br>143.10 |

| | ¹H—NMR | | | | | ¹³C—NMR | | | | |
|---|---|---|---|---|---|---|---|---|---|---|
| Compnd | C₄H₈— | —(CH₂)₄— | —(CH₂)ₙ— | aromatic | aromatic | C₄H₈— | —(CH₂)₄— | —(CH₂)ₙ— | aromatic | aromatic |
| 20d | J = 6.83<br>0.14, m<br>0.47, m<br>0.83, quin | J = 7.32<br>1.58, m<br>3.12, t<br>3.22, t | 1.26, quin<br>1.50, quin<br>3.06, t | 2.41, s<br>2.42, s<br>7.28, d | 7.30, d<br>7.67, d<br>J = 8.30 | 4.17<br>9.87<br>52.88 | 25.76<br>25.84<br>47.35 | 26.30<br>28.71<br>48.35 | 21.48<br>127.05<br>129.60 | 136.79<br>137.07<br>143.00 |

-continued

| | $^1$H—NMR | | | | | $^{13}$C—NMR | | | | |
|---|---|---|---|---|---|---|---|---|---|---|
| Compnd | C$_4$H$_8$— | —(CH$_2$)$_4$— | —(CH$_2$)$_n$— | aromatic | aromatic | C$_4$H$_8$ | —(CH$_2$)$_4$— | —(CH$_2$)$_n$— | aromatic | aromatic |
| | 2.99, d J = 6.83 | J = 7.32 | J = 7.32 | J = 8.30 | | | 47.84 | | 129.65 | 143.06 |
| 20e | 0.14, m 0.47, m 0.83, quin 2.99, d J = 6.83 | 1.57~ 1.58, m 3.12, t 3.22, t J = 7.32 | 1.25, quin 1.50, quin 3.06, t J = 7.32 | 2.41, s 2.42, s 7.28, d J = 8.30 | 7.30, d 7.67, d | 4.16 9.87 52.88 | 25.79 25.83 47.35 47.81 | 26.65 28.71 48.44 | 21.47 127.05 129.60 | 136.84 137.09 142.98 143.03 |
| 20f | 0.14, m 0.48, m 0.83, quin 2.99, d J = 6.83 | 1.59, m 3.12, t 3.22, t J = 7.32 | 1.24, m 1.49, quin 3.06, t J = 7.32 | 2.42, s 2.42, s 7.28, d J = 8.30 | 7.29, d 7.67, d J = 8.30 | 4.17 9.87 52.88 | 25.78 25.83 47.35 47.78 | 26.65 28.74 29.12 48.44 | 21.48 127.05 129.60 | 136.88 137.09 143.00 143.03 |
| 20g | 0.15, m 0.49, m 0.83, quin 2.99, d J = 6.83 | 1.57, m 3.12, t 3.22, t J = 7.32 | 1.23, m 1.49, quin 3.06, t J = 7.32 | 2.41, s 2.42, s 7.29, d 7.67, d J = 8.30 | | 4.16 9.88 52.88 | 25.78 25.83 47.37 47.74 | 26.72 28.74 29.12 29.45 48.44 | 21.48 127.04 129.60 | 136.89 137.11 143.01 |
| 20h | 0.15, m 0.48, m 0.83, quin 2.99, d J = 6.83 | 1.57, m 3.12, t 3.22, t J = 7.32 | 1.23, m 1.49, quin 3.06, t J = 7.32 | 2.42, s 7.28, d 7.29, d 7.68, d J = 8.30 | | 4.16 9.88 52.86 | 25.78 25.83 47.35 47.71 | 26.77 28.74 29.18 29.45 48.44 | 21.48 127.07 129.60 | 136.89 137.09 143.00 |

| | $^1$H—NMR | | | | | $^{13}$C—NMR | | | |
|---|---|---|---|---|---|---|---|---|---|
| Compnd | Et | —(CH$_2$)$_4$— | —(CH$_2$)$_3$— | NH—CHO/aromatic | | Et | —(CH$_2$)$_4$— | —(CH$_2$)$_3$— | NH—CHO/aromatic |
| 23 | 1.07, t 3.19, quar J = 7.32 | 1.60, quin 1.67, quin 3.10, t 3.18, t 3.34, quar J = 7.32 | 1.86, quin 3.14, t | 2.43, s 6.05, bs 7.31, d | 7.66, d 7.67, d 8.16, bs J = 8.30 | 13.91 43.40 | 26.39 37.36 49.08 | 28.23 45.54 46.92 | 21.48 127.04 127.12 129.77 135.91 | 136.37 143.39 143.43 161.44 |

| Compnd | C$_4$H$_8$— | —(CH$_2$)$_4$— | —(CH$_2$)$_3$— | NH-CHO/aromatic | | C$_4$H$_8$ | —(CH$_2$)$_4$— | —(CH$_2$)$_3$— | NH-CHO/aromatic | |
|---|---|---|---|---|---|---|---|---|---|---|
| 24 | 0.16, m 0.50, m 0.82, quin 2.99, d J = 6.83 | 1.59, quin 1.67, quin 3.10, t 3.34, t J = 7.32 | 1.96, quin 3.17, t 3.26, t | 2.43, s 6.04, bs 7.31, d | 7.66, d 8.16, bs J = 8.30 | 4.19 9.87 53.60 | 26.34 26.37 37.35 48.98 | 29.18 46.16 46.94 | 21.48 127.04 127.12 129.75 136.00 | 136.37 143.34 143.39 161.46 |

| Compnd | Et | —(CH$_2$)$_3$— | | aromatic | aromatic | Et | —(CH$_2$)$_3$— | | aromatic | aromatic |
|---|---|---|---|---|---|---|---|---|---|---|
| 28 | 1.06, t 3.16, quar J = 7.32 | 1.70, quin 3.12, t J = 7.32 | | 2.42, s 3.49, s 7.26, d 7.66, d J = 8.30 | | 14.10 42.87 | 26.67 45.97 | | 21.47 51.25 58.59 126.89 127.05 | 128.21 128.77 129.59 137.07 142.92 |

| Compnd | C$_4$H$_8$ | —(CH$_2$)$_3$— | | aromatic | aromatic | C$_4$H$_8$ | —(CH$_2$)$_3$— | | aromatic | aromatic |
|---|---|---|---|---|---|---|---|---|---|---|
| 29 | 0.14, m 0.46, m 0.83, quin 2.98, d J = 6.83 | 1.76, quin 3.12, t J = 7.32 | | 2.40, s 3.49, s 7.26, d 7.66, d | | 4.11 9.98 52.93 | 26.60 46.41 | | 21.47 51.28 58.47 128.17 | 128.75 129.55 137.21 142.88 |

| Compnd | Et | —(CH$_2$)$_3$— | —(CH$_2$)$_3$— | aromatic | aromatic | Et | —(CH$_2$)$_3$— | —(CH$_2$)$_3$— | aromatic | aromatic |
|---|---|---|---|---|---|---|---|---|---|---|
| 33 | 1.05, t 3.16, quar J = 7.32 | 1.69, quin 3.11, t J = 7.32 | 1.83, quin 3.14, t J = 7.32 | 2.41, s 3.46, s 7.27, d 7.64, d J = 8.30 | 7.65, d J = 8.30 | 13.91 43.14 | 26.58 45.47 47.38 | 28.69 46.49 | 21.47 51.12 58.46 126.89 127.07 | 127.12 128.77 129.70 136.35 143.29 |

| | ¹H—NMR | | | | | ¹³C—NMR | | | | |
|---|---|---|---|---|---|---|---|---|---|---|
| Compnd | $C_4H_8$ | —$(CH_2)_3$— | —$(CH_2)_3$— | aromatic | aromatic | $C_4H_8$ | —$(CH_2)_3$— | —$(CH_2)_3$— | aromatic | aromatic |
| 34 | 0.14, m<br>0.46, m<br>0.81, quin<br>2.98, d<br>J = 6.83 | 1.69, quin<br>3.11, t<br>3.12, t<br>J = 7.32 | 1.90, quin<br>3.20, t<br>J = 7.32 | 2.40, s<br>3.46, s<br>7.27, d<br>7.64, d<br>J = 8.30 | | 4.16<br>9.82<br>53.27 | 26.49<br>45.87<br>47.28 | 28.72<br>46.51 | 21.47<br>51.10<br>58.42<br>126.89<br>127.07 | 127.12<br>128.22<br>128.77<br>129.64<br>129.69<br>136.75<br>143.06 |
| Compnd | Et | —$(CH_2)_4$— | —$(CH_2)_3$— | aromatic | aromatic | Et | —$(CH_2)_4$— | —$(CH_2)_3$— | aromatic | aromatic |
| 38 | 1.04, t<br>3.15, quar<br>J = 7.32 | 1.54, quin<br>3.10, t<br>J = 7.32 | 1.64, quin<br>3.10, t<br>J = 7.32 | 2.41, s<br>3.46, s<br>7.27, d<br>7.64, d<br>J = 8.30 | 7.66, d<br>J = 8.30 | 14.00<br>42.78 | 25.73<br>26.58<br>46.94 | 28.69<br>47.97 | 21.47<br>51.20<br>58.41<br>127.04<br>127.09<br>128.22 | 128.75<br>129.62<br>129.67<br>137.03<br>143.00<br>143.08 |
| Compnd | $C_4H_8$ | —$(CH_2)_4$— | —$(CH_2)_3$— | aromatic | aromatic | $C_4H_8$ | —$(CH_2)_4$— | —$(CH_2)_3$— | aromatic | aromatic |
| 39 | 0.13, m<br>0.45, m<br>0.80, quin<br>2.97, d<br>J = 6.83 | 1.57, m<br>3.08, t<br>3.19, t<br>J = 7.32 | 1.65, quin<br>3.08, t<br>J = 7.32 | 2.40, s<br>3.46, s<br>7.27, d<br>7.64, d<br>J = 8.30 | 7.66, d<br>J = 8.30 | 4.16<br>9.85<br>52.86 | 25.78<br>26.57<br>46.86<br>47.32 | 28.69<br>47.97 | 21.47<br>51.18<br>58.37<br>127.05<br>127.09<br>128.21 | 128.75<br>129.59<br>129.65<br>136.73<br>137.11<br>142.95<br>143.05 |

Example 14

Assay Method for Anticancer Effect

Each assay compound was added to an HCC panel comprising a variety of cancer cells to measure a concentration of compound at which cancer cell proliferation showed a certain level. The anticancer effect of each compound was determined by using the obtained concentration.

The anticancer effect assay was performed for the following three compounds: Compound 15f synthesized in Example 3.6 (1,18-bis(ethylamino)-5,14-diazaoctadecane, referred to as BET484 hereinafter), Compound 21d synthesized in Example 6.4 (1,16-bis(cyclopropylmethylamino)-5,12-diazahexadecane, referred to as BCPM464 hereinafter) and Compound 21e synthesized in Example 6.5 (1,17-bis(cyclopropylmethylamino)-5,13-diazahexadecane, referred to as BCPM474 hereinafter).

For the assay of anticancer effect, used was an HCC panel comprising 39 cell lines in total: 7 cell lines of lung cancer (Lu), 6 cell lines of stomach cancer (St), 5 cell lines of colon cancer (Co), 5 cell lines of ovarian cancer (Ov), 6 cell lines of brain tumor (CNS), 5 cell lines of breast cancer (Br), 2 cell lines of renal cancer (Re), 2 cell lines of prostate cancer (xPg) and 1 cell line of melanoma (Me). These were used as one panel, and an in-vitro drug sensitivity test was performed by using the above three compounds to obtain sensitivity patterns against each compound (mean graphs mentioned below). Further, the mean graphs obtained as the results of the above sensitivity test were compared with data in a database.

Specifically, the drug sensitivity test was performed according to the following procedures. The above 39 cancer cell lines were seeded to a 96-well plate and incubated overnight. On the following day, sample solutions each containing each of the above three compounds (5 doses, usually from $10^{-4}$ M to $10^{-8}$ M with 1 log intervals, the highest concentration is referred to as "High Conc") were added to the above 96-well plate and cultured for further 2 days. Subsequently, the cell proliferation was calorimetrically determined in the obtained plate by using Sulfo Rhodamine B.

The obtained data of the measurement results are shown as mean graphs. Mean graphs (also referred to as fingerprints) visually expresses effective concentration deviations of a sample substance against individual cancer cell lines so that the sensitivity of each cancer cell line against the sample can be recognized at a glance. The mean graph is also referred to as fingerprint because it represents a pattern unique to each drug.

In the data analysis, GI50 (concentration at which cell proliferation is inhibited to 50% of a control) is obtained as a parameter for data analysis using the cell number immediately before exposure of cells to the test compound (Time Zero) as a standard. Specifically, the obtained data is used for the following calculation:

1) If a mean optical density value at each concentration (OD test) is larger than the OD value at Time Zero (Tz), i.e., OD test>Tz, then percent growth (PG%)=((OD test−Tz)/(OD control−Tz))×100, wherein 1 OD control is the OD value of control. On the contrary, if OD test<Tz, then PG%=((OD test−Tz)/Tz)×100. In this case, PG % is a negative value.

2) The above PG % values obtained for each cell line are plotted against concentrations (logarithm) according to the organ cancer type. The concentration at the point where each curve intersects with a horizontal line, provided at PG 50%, corresponds to log GI50.

3) Then, "mean graphs" are created. Mean log GI50 values are obtained for all of the assayed cell lines and referred to as mean graph midpoints (MG-MID). A difference between each of the mean values and the log GI50 value for each cell line is obtained (that is, GI50 for each cell line is represented as a logarithmic value of a multiple or an aliquot of the mean value). The resulting differences are depicted as bar charts extending a left or right side from the center line of mean log GI50 (scale 0) to obtain a mean graph. The higher differential sensitivity a cell line has, the longer the bar extends to the right. One scale corresponds to 1 log. The value of "Delta" provided at the bottom of the mean graph represents the difference between the value for the most sensitive cell line and the mean value. The value of "Range" provided below "Delta" represents the difference between the log GI50 values of the most sensitive cell line and the least sensitive one. If such data cannot be obtained within the range of concentrations tested, the "limit" values (usually, −4 is used as the upper limit and −8 is used as the lower limit) are used alternatively (these value are referred to as false values, the number of which is shown in Summary of Evaluation, and the upper limit value and the lower limit value of which are shown under "High" and "Low", respectively). Thus, the mean values calculated here are not necessarily the exact mean values, and therefore a term "mean graph midpoint (MG-MID)" is used instead of "mean value".

Evaluation Criteria

The obtained mean graphs were evaluated as for possibility as an anticancer agent with further consideration of the following points. The evaluation might be difficult since the results were represented as a mean graph. However, it was evaluated if each sample compound was highly interesting or not as an anticancer agent mainly considering the following points.

A. Novelty of the chemical structure.
B. Strength of proliferation inhibition (average effective concentration, cytocidal effect). As a criterion of effective concentration, a sample compound was determined effective, if MG-MID <−5.
C. Differential activity (whether marked efficacy can be observed against a specific cancer type or some cancer cell lines). As a criterion of differential activity, a sample compound was determined effective, if Delta ≧0.5 and Range ≧1.
D. Uniqueness of the fingerprint.

The mean graphs of the sample substances were compared with all of the existent anticancer agents in a database by using the COMPARE program. Based on the r value (rmax) of the anticancer drug (Drug A) that exhibited the highest r value (the value closest to 1), evaluation was made as follows:

(1) If rmax <0.5, then the sample is determined to be "COMPARE Negative". If no existent anticancer agent in the database has a mean graph similar to that of the sample substance, a novel action mechanism can be expected.

(2) If 0.5≦rmax <0.75, then the sample is determined to be "COMPARE Marginal". The mean graph of the sample is somewhat similar to that of Drug A. In other words, it is possible that the sample has a similar action mechanism as that of Drug A, while it is also possible that the sample has a novel action mechanism. This is the case between (1) and (3).

(3) If 0.75≦rmax, then the sample is determined to be "COMPARE Positive". The mean graph of the sample is very similar to that of Drug A. In other words, the same action mechanism as that of Drug A is expected.

Usually, samples are required to satisfy A, B and C. Then, the samples that have been determined to be "COMPARE Negative" are considered to have a possibility of having a novel action mechanism and given with preference. Therefore, a sample is regarded as "the most interesting", if it satisfies A, B and C and is determined to be "COMPARE Negative".

Assay Results

As a result of a series of the above assays and evaluations, the three compounds, BET484, BCPM464 and BCPM474, were judged to be "the most interesting". This evaluation suggested that these three compounds had good potentiality as an anticancer agent. Table 14 and FIG. 1 (mean graph) mentioned below show GI50 values for cultured human cancer cell lines (concentration at which cell proliferation is inhibited to 50% of the control, represented with logarithmic values of molar concentration)

TABLE 14

Anticancer effect on cultured human cancer cell lines used (the values are represented as log GI50 (molar concentration). Figures are omitted if log GI50 ≧ −4.00 for legibility)

| Cell line* | BET484 (JCI-10876) | BCPM464 (JCI-10878) | BCPM474 (JCI-10879) |
|---|---|---|---|
| MG-MID (< −5) | −4.17 | −4.86 | −4.94 |
| Delta (≧ 0.5) | 1.45 | 1.19 | 0.84 |
| Range (≧ 1.0) | 1.62 | 2.05 | 1.76 |
| HBC-4 (Br) | | −5.16 | −5.34 |
| BSY-1 (Br) | | −5.45 | −5.15 |
| HBC-5 (Br) | | −6.05 | −5.65 |
| MCF-7 (Br) | | −4.86 | −4.25 |
| MDA-MB-231 (Br) | | | |
| U251 (CNS) | | −4.22 | |
| SF-268 (CNS) | | −4.06 | −5.33 |
| SF-295 (CNS) | | | −5.06 |
| SF-539 (CNS) | −5.10 | −5.50 | −5.46 |
| SNB-75 (CNS) | −4.89 | −5.48 | −5.44 |
| SNB-78 (CNS) | | | |
| HCC2998 (Co) | | −4.20 | −4.99 |
| KM-12 (Co) | | | −4.55 |
| HT-29 (Co) | | −4.63 | −5.06 |
| HCT-15 (Co) | | | −4.43 |
| HCT-116 (Co) | | −5.17 | −5.16 |
| NCI-H23 (Lu) | | −5.45 | −5.36 |
| NCI-H226 (Lu) | | −5.14 | −5.04 |
| NCI-H522 (Lu) | | −5.74 | −5.49 |
| NCI-H460 (Lu) | | −5.01 | −4.78 |
| A549 (Lu) | −4.79 | −5.55 | −5.55 |
| DM5273 (Lu) | −5.52 | −5.36 | −5.38 |
| DMS114 (Lu) | | −5.36 | −5.42 |
| LOX-IMVI (Me) | | −5.20 | −4.51 |
| OVCAR-3 (Ov) | −4.70 | −5.52 | −5.78 |
| OVCAR-4 (Ov) | −5.23 | −5.54 | −5.38 |
| OVCAR-5 (Ov) | −4.14 | −5.36 | −5.27 |
| OVCAR-8 (Ov) | | −5.24 | −5.56 |
| SK-OV-3 (Ov) | | | −5.24 |
| RXF-631L (Re) | | | |
| ACHN (Re) | | | |
| St-4 (St) | | −5.19 | −5.16 |
| MKN1 (St) | | −5.14 | −4.92 |
| MKN7 (St) | | −5.38 | −5.36 |
| MKN28 (St) | | −5.33 | −5.28 |
| MKN45 (St) | | −5.19 | −4.92 |
| MKN74 (St) | | | −4.32 |
| DU-145 (xPg) | | | −4.17 |
| PC-3 (xPg) | | | |

*Original tissues of the cell lines are given in parentheses: breast cancer (Br), brain tumor (CNS), colon cancer (Co), lung cancer (Lu), melanoma (Me), ovarian cancer (Ov), renal cancer (Re), stomach cancer (St), and prostate cancer (xPg). The JCI numbers in parentheses refer to compound registration numbers in CCC.

Relationship Between the Screening Results and In Vivo Effect

It is not easy to determine what extent the log GI50 values obtained in the in vitro experiment, listed in Table 14 "Anticancer effect on cultured human cancer cell lines used", represent in vivo efficacy of the compounds as an anticancer agent by using only the values provided herein. Therefore, a reference is exemplified below, which can be used as the basis for verifying the anticancer effect represented by the above assay results.

Out of samples screened according to the above method by the Chemotherapy Center of the Japanese Foundation for Cancer Research, the screening results of 305 samples are summarized in "Cancer and Chemotherapy", 21 (9), pp.1512–1554 (1994). Essential points of the results obtained by converting the concentrations shown in the above reference to log GI50 are as follows. First, in vitro distributions of log GI50 for 5 of human gastric cancer cell lines and P388 mouse leukemia cells randomly collected from general samples were sorted out according to value ranges of log GI50, and shown in the following Table 15.

TABLE 15

Distribution of log GI50 values for various cell lines (in vitro, % in 305 samples)

| log GI50 (M) | MKN-1 | MKN-28 | MKN-45 | NUGC-3 | St-4 | P388 |
|---|---|---|---|---|---|---|
| $-4 \leq$ log GI50 | 34 | 33 | 34 | 28 | 36 | 21 |
| $-5 \leq$ log GI50 $\leq -4$ | 29 | 30 | 25 | 26 | 26 | 21 |
| $-6 \leq$ log GI50 $\leq -5$ | 26 | 26 | 23 | 30 | 28 | 25 |
| $-7 \leq$ log GI50 $\leq -6$ | 5 | 6 | 13 | 9 | 4 | 22 |
| log GI50 $\leq -7$ | 6 | 5 | 5 | 7 | 5 | 11 |

It is shown that 37 to 46% of the samples satisfied log GI50<-5 in 5 of the gastric cancer cell lines. Furthermore, only 9 to 18% of all of the samples satisfied log GI50<-6.

In vitro effect and in vivo effect on P388 mouse leukemia cells were compared for 93 samples out of these. The results are summarized in Table 16.

TABLE 16

Comparison of in vitro effect and in vivo effect on P388 mouse leukemia cells

| in vitro | in vivo Positive | in vivo Negative |
|---|---|---|
| $-4 \leq$ log GI50 | 0% | 100% |
| $-5 \leq$ log GI50 $\leq -4$ | 31 | 69 |
| $-6 \leq$ log GI50 $\leq -5$ | 47 | 53 |
| $-7 \leq$ log GI50 $\leq -6$ | 55 | 45 |
| log GI50 $\leq -7$ | 82 | 18 |

Since the comparison has not been performed for human lung cancer cell lines, the following is inferred only from the results on P388 cells. All of the compounds satisfying $-4 \leq$ log GI50 in vitro were ineffective in vivo. It is indicated that, if a compound exhibits strong activity in vitro, the compound is highly likely to have in vivo activity. It can also be considered that the invitro threshold enabling one to expect in vivo activity is log GI50<-4. The in vivo positive value would exceed 50%, if log GI50<-5 or -6.

Discussion of Results

From the results shown in Table 14 and the mean graph shown in FIG. 1, it is clear that BET484, BCPM464 and BCPM474 satisfy log GI50<-4 for many cancer cell lines. From the comparison of the result obtained in the HCC panel and the experimental results of the relationship as to in vivo effect (Tables 15 and 16), it was revealed that the compounds that showed in vitro HCC panel results satisfying log GI50<-4 would highly possibly exert in vivo anticancer activity. Therefore, it became clear that BET484, BCPM464 and BCPM474, which satisfied log GI50<-4 in the mean graphs as the results in HCC panel, were those compounds highly possibly exerting in vivo anticancer activity.

What is claimed is:

1. A compound represented by the following formula (I) or a pharmaceutically acceptable salt thereof

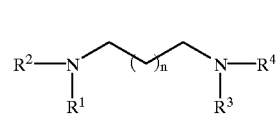
(I)

wherein:

n is an integer of 1–8, $R^1$ represents a hydrogen atom or a p-toluenesulfonyl group, $R^2$ represents a group represented by the following Formula (II), $R^3$ represents a hydrogen atom or a p-toluenesulfonyl group, and $R^4$ represents a group represented by the following Formula (II):

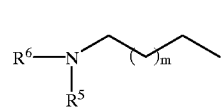
(II)

where m is 1 or 2, $R^5$ represents a hydrogen atom or a p-toluenesulfonyl group, and $R^6$ represents a cyclopropylmethyl group.

2. The compound or a pharmaceutically acceptable salt thereof according to claim 1, wherein $R^1$ and $R^3$ represent a hydrogen atom, and $R^5$ represents a hydrogen atom.

3. An anticancer agent which contains, as an active ingredient, at least one of the compound represented by Formula (I) according to claim 1 and/or a pharmaceutically acceptable salt thereof.

4. An anticancer agent, which contains, as an active ingredient, 1,1 6-bis(cyclopropyl-methylamino)-5,12-diazaliexadecane and/or a pharmaceutically acceptable salt thereof.

5. The compound or a pharmaceutically acceptable salt thereof according to claim 1, wherein said compound represented by the following formula (I) is 1,16-bis(cyclopropylmethylamino)-5,12-diazahexadecane.

6. The compound or a pharmaceutically acceptable salt thereof according to claim 1, wherein said compound represented by the following formula (I) is 1,17-bis(cyclopropylmethylamino)-5,13-diazaheptadecane.

7. An anticancer agent which contains, as an active ingredient, 1,17-bis(cyclopropylmethylamino)-5,13-diazaheptadecane and/or a pharmaceutically acceptable salt thereof.

* * * * *